United States Patent
Wu et al.

(10) Patent No.: US 10,355,226 B2
(45) Date of Patent: Jul. 16, 2019

(54) BORON-CONTAINING COMPOUND, EMITTING LAYER OF ORGANIC LIGHT EMITTING DIODE AND ORGANIC LIGHT EMITTING DIODE DEVICE

(71) Applicant: NATIONAL TSING HUA UNIVERSITY, Hsinchu (TW)

(72) Inventors: Tien-Lin Wu, Hsinchu (TW); Chih-Chun Lin, Hsinchu (TW); Rai-Shung Liu, Hsinchu (TW); Chien-Hong Cheng, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 91 days.

(21) Appl. No.: 15/343,199

(22) Filed: Nov. 3, 2016

(65) Prior Publication Data
US 2018/0013064 A1 Jan. 11, 2018

(30) Foreign Application Priority Data
Jul. 11, 2016 (TW) .............................. 105121773 A

(51) Int. Cl.
| | | |
|---|---|---|
| H01L 51/00 | (2006.01) | |
| C07F 5/02 | (2006.01) | |
| C09K 11/02 | (2006.01) | |
| C09K 11/06 | (2006.01) | |
| H01L 51/50 | (2006.01) | |

(52) U.S. Cl.
CPC ............ *H01L 51/008* (2013.01); *C07F 5/027* (2013.01); *C09K 11/025* (2013.01); *C09K 11/06* (2013.01); *H01L 51/0059* (2013.01); *H01L 51/0071* (2013.01); *H01L 51/0072* (2013.01); *H01L 51/0074* (2013.01); *C09K 2211/1007* (2013.01); *C09K 2211/1014* (2013.01); *C09K 2211/1029* (2013.01); *C09K 2211/1096* (2013.01); *H01L 51/5012* (2013.01); *H01L 51/5028* (2013.01); *H01L 2251/552* (2013.01)

(58) Field of Classification Search
CPC combination set(s) only.
See application file for complete search history.

(56) References Cited

PUBLICATIONS

Chou and Cheng, A Highly Efficient Universal Bipolar Host for Blue, Green, and Red Phosphorescent OLEDs, Advanced Materials, Jun. 2010, 22, 2468-71. (Year: 2010).*
Durka et al., Efficient 8-Oxyquinolinato emitters based on a 9,10-dihydro-9,10-diboraanthracene scaffold for applications in optoelectronic devices, J. Mater. Chem., Nov. 2014, 3, 1354. (Year: 2014).*
Lorbach et al. Dilithio 9,10-diborataanthracene: Molecular Structure and 1,4-addition Reactions, Organometallics, Oct. 2010, 29, 5762-5765. (Year: 2010).*

(Continued)

*Primary Examiner* — Jennifer A Chriss
*Assistant Examiner* — Sean M DeGuire
(74) *Attorney, Agent, or Firm* — CKC & Partners Co., LLC

(57) ABSTRACT

The present disclosure relates to a boron-containing compound including a structure of Formula (I), and the use of the compound as a dopant in an emitting layer of an organic light emitting diode. The present disclosure also relates to an emitting layer of an organic light emitting diode and an organic light emitting diode device.

7 Claims, 27 Drawing Sheets

(56) References Cited

PUBLICATIONS

Agou et al., Stepwise syntehsis and properties of a 9,10-dihydro-9,10-diboraanthracene, Tetrahedron Letters, 51, Jul. 2010, 5013-5015. (Year: 2010).*

Bieller et al., Bitopic Bis- and Tris(1-pyrazolyl)borate Ligands: Syntehsis and Structural Characterization, Organometallics, Mar. 2004, 23, 2107-2113. (Year: 2004).*

Claas Hoffend et al., "Effects of boron doping on the structural and optoelectronic properties of 9,10-diarylanthracenes", Dalton Transactions, published on Oct. 14, 2013, issue 38, pp. 13826-13837, published by The Royal Society of Chemistry, England.

Rainer Stahl et al., "Electrochemistry and Photophysics of Donor-Substituted Triarylboranes: Symmetry Breaking in Ground and Excited State", Chemistry—A European Journal, published on Mar. 1, 2006, vol. 12, issue 8, pp. 2358-2370, published by Wiley-VCH, Germany.

Ye Tao et al., "Thermally Activated Delayed Fluorescence Materials Towards the Breakthrough of Organoelectronics", Advanced Materials, published on Dec. 17, 2014, vol. 26, issue 47, pp. 7931-7958, published by Wiley-VCH Verlag GmbH & Co. KGaA, Germany.

Zhenyu Zhang et al., "Diboron complexes with bis-spiro structures as high-performance blue emitters for OLEDs", Dalton Transactions, published on Aug. 28, 2015, vol. 44, issue 32, pp. 14436-14443, published by Royal Society of Chemistry, United Kingdom.

Christian Reus et al., "C-Functionalized, Air- and Water-Stable 9,10-Dihydro-9,10-diboraanthracenes: Efficient Blue to Red Emitting Luminophores", Journal of the American Chemical Society, published on Aug. 28, 2013, vol. 135, issue 34, pp. 12892-12907, published by American Chemical Society, United States.

Claas Hoffend et al., "Boron-Doped Tri(9,10-anthrylene)s: Synthesis, Structural Characterization, and Optoelectronic Properties", Chemistry—A European Journal, published on Nov. 26, 2012, vol. 18, issue 48, pp. 15394-15405, published by Wiley-VCH Verlag GmbH & Co. KGaA, Germany.

* cited by examiner

BORON-CONTAINING COMPOUND, EMITTING LAYER OF ORGANIC LIGHT EMITTING DIODE AND ORGANIC LIGHT EMITTING DIODE DEVICE

RELATED APPLICATIONS

This application claims priority to Taiwan Application Serial Number 105121773, filed Jul. 11, 2016, which is herein incorporated by reference.

BACKGROUND

Technical Field

The present disclosure relates to a boron-containing compound, an emitting layer of an organic light emitting diode (OLED) and an OLED device. More particularly, the present disclosure relates to a boron-containing compound which can be used as a dopant of an emitting layer of an OLED, and an emitting layer of an OLED and an OLED device having the same.

Description of Related Art

An OLED refers to a component having an emitting layer made of organic molecules, which can emit light in response to a driving voltage. Comparing to a liquid crystal display, the OLED has advantages of lighter weight, wider view angle, higher contrast ratio, lower power consumption, faster response times, high luminous efficiency, facile color tuning of emitters, access to flexible panels. Accordingly, the OLED draws lots of attention from the relevant industry.

The earliest OLED adopts fluorescence materials, in which excitons can transition from a singlet excited state to a singlet ground state and release energy in the form of fluorescence. However, the internal quantum efficiency (IQE) of fluorescence materials can only reach to 25%, and the rest of 75% is lost in the non-radiative form of heat. Accordingly, the efficiency of the fluorescence material is poor.

Then the OLED adopting phosphorescence materials is provided, in which noble metals, such as Ir, Pt, Os and Ru, are introduced into the emitting layer to form complexes with organic molecules so as to generate the effect of spin-orbital coupling. As a result, the fluorescence generated from the transition from the singlet excited state to the singlet ground state and the phosphorescence generated from the transition from a triplet excited state to the singlet ground state can be obtained at the same time, so that the IQE of phosphorescence materials can reach to 100%. Introducing the noble metals into the emitting layer increases the efficiency of the OLED significantly. However, the noble metals are expansive, so that the cost of the phosphorescence materials remains stubbornly high. Furthermore, blue OLEDs still cannot be manufactured with the phosphorescence materials.

Thermal activated delayed fluorescence (TADF) materials are the third generation organic light emitting materials, which are developed after the fluorescence materials and the phosphorescence materials. The energy gap of the singlet excited state and the triplet excited state ($\Delta E_{ST}$) of the TADF materials is small, which allows excitons to transition from the triplet excited state to the singlet excited state through reverse intersystem crossing (RISC). Therefore, the TADF materials can take advantage of the excitons in singlet excited state and triplet excited state releasing energy in radiative form (fluorescence and delayed fluorescence), which enables the IQE of the TADF materials to reach to 100%. The TADF materials are featured with high efficiency, low cost (due to no use of noble metals) and can provide a wide light color tunability (capable of manufacturing blue OLEDs). Accordingly, the TADF materials have received lots of attention.

However, the OLEDs made of the TADF materials are hardly to provide an external quantum efficiency (EQE) comparable to that of the phosphorescence materials. Researches show that the molecular structure of the TADF material is critical to the performance of the OLEDs. For example, it is realized that in molecules with a small overlap between their highest occupied molecular orbital (HOMO) bearing electron donating groups and lowest unoccupied molecular orbital (LUMO) bearing electron accepting groups can increase the TADF property. Furthermore, by increasing the twist angle between a plane of the electron donating group and a plane of the electron accepting group can lower the $\Delta E_{ST}$, which can increase the probability of RISC. However, an excessive twist angle may inhibit the radiative decay of the transition from the singlet excited state to the singlet ground state, which reduces the luminous efficiency.

Moreover, among many compounds, boron-containing compound has a vacant p orbital which can interact with the surrounding π-electron clouds, and thus is regarded as a promising candidate for the organic light emitting materials. However, the IQEs of the boron-containing compounds developed to date rarely exceed 30%, and the boron-containing compounds have the drawback of high sensitivity toward air and moisture, both of which impede the boron-containing compounds to be applied to the organic light emitting materials.

To sum up, how to improve the molecular structure of the boron-containing compounds, in which the electron donating groups and the electron accepting groups are properly arranged so as to feature the boron-containing compounds with TADF properties (i.e., the IQE is 100%), and accordingly can break through the impediment in the application of the organic light emitting materials and provide the OLEDs with excellent efficiency, is the goal of the relevant industry and academia.

SUMMARY

According to one aspect of the present disclosure, a boron-containing compound includes a structure of Formula (I):

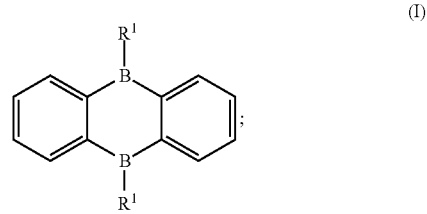

wherein each $R^1$ is independently an electron donating group.

According to another aspect of the present disclosure, an emitting layer of an OLED includes a dopant, and the dopant includes a structure of Formula (i):

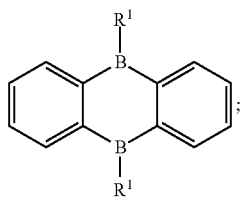

(I)

wherein each R¹ is independently an electron donating group.

According to yet another aspect of the present disclosure, an OLED device includes the aforementioned emitting layer of the OLED.

BRIEF DESCRIPTION OF THE DRAWINGS

The present disclosure can be more fully understood by reading the following detailed description of the embodiment, with reference made to the accompanying drawings as follows.

DETAILED DESCRIPTION

Boron-Containing Compound

A boron-containing compound includes a structure of Formula (I):

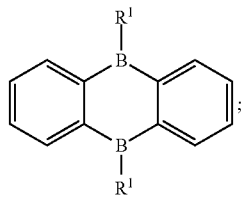

(I)

wherein each R¹ is independently an electron donating group.

For the sake of conciseness, "the boron-containing compound including the structure of Formula (I)" is also expressed as "the boron-containing compound (I)" in the present disclosure, and the expression can be applied to other compounds.

With the structure of Formula (I), the boron-containing compound has 9,10-diboraanthracene (DBA) being an electron accepting group and R¹ being an electron donating group, which features the boron-containing compound (I) with TADF property. When the boron-containing compound (I) is driven by a proper voltage, the boron-containing compound (I) can release energy in the form of fluorescence and delayed fluorescence. Therefore, it is favorable to use the boron-containing compound (I) as a dopant in an emitting layer of an OLED, which can provide the OLED with advantages of high efficiency, low cost and capable of providing a wide light color tenability.

Specifically, the two R's in Formula (I) can be the same or different. Each R¹ can be independently a structure of Formula (i) or a structure of Formula (ii):

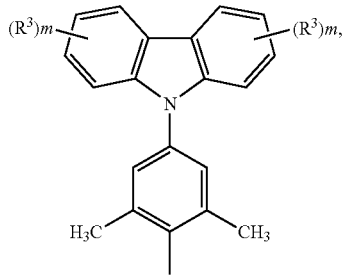

(i)

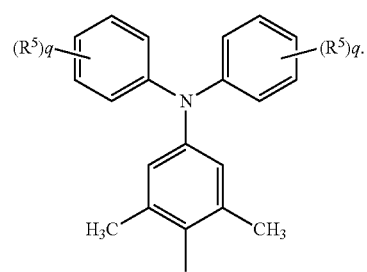

(ii)

In Formula (i), each m can be independently an integer of 0 to 4. When m equals to 0, hydrogen atoms of the two benzene rings in the upper part of Formula (i) are unsubstituted. When m equals to an integer of 1 to 4, 1 to 4 hydrogen atoms of the two benzene rings in the upper part of Formula (i) can be substituted by R³. R³ can be but is not limited to a methoxy group or a tert-butyl group. When a number of R³s in Formula (i) is greater than 1, a plurality of R³s can be the same or different.

In Formula (ii), each q can be independently an integer of 0 to 4. When q equals to 0, hydrogen atoms of the two benzene rings in the upper part of Formula (ii) are unsubstituted. When q equals to an integer of 1 to 4, 1 to 4 hydrogen atoms of the two benzene rings in the upper part of Formula (ii) can be substituted by R⁵. R⁵ can be but is not limited to a methoxy group or a tert-butyl group. When a number of R⁵s in Formula (ii) is greater than 1, a plurality of R⁵s can be the same or different.

According to the aforementioned boron-containing compound (I), each m can be independently an integer of 0 to 1, and each q can be independently an integer of 0 to 1. That is, each R¹ can be independently a structure of Formula (i-1-1), a structure of Formula (i-2-1), a structure of Formula (ii-1-1) or a structure of Formula (ii-2-1):

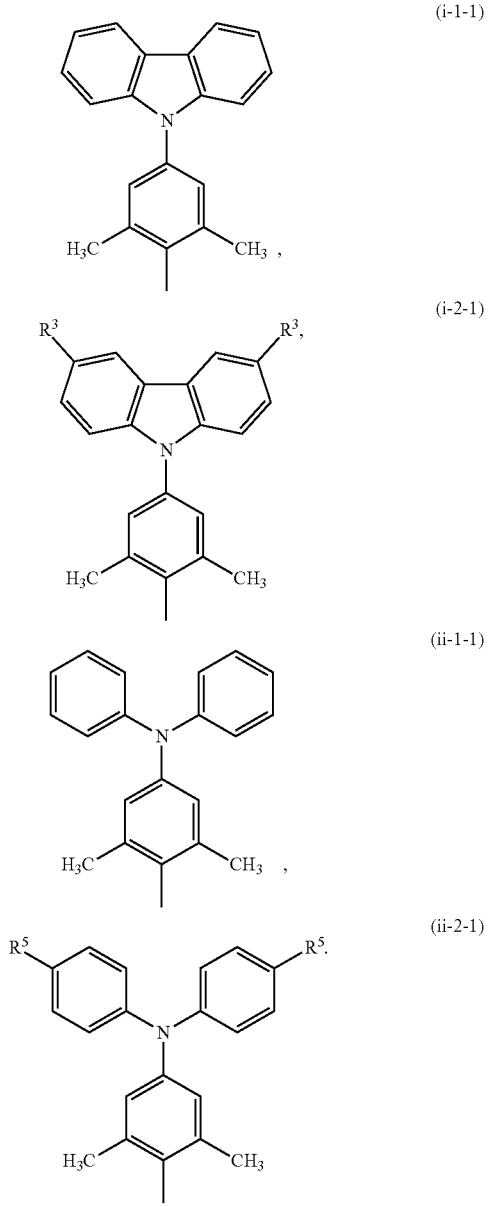

The definitions of R³ and R⁵ have been recited previously, and will not be repeated herein.

Emitting Layer of OLED

Figure 1:
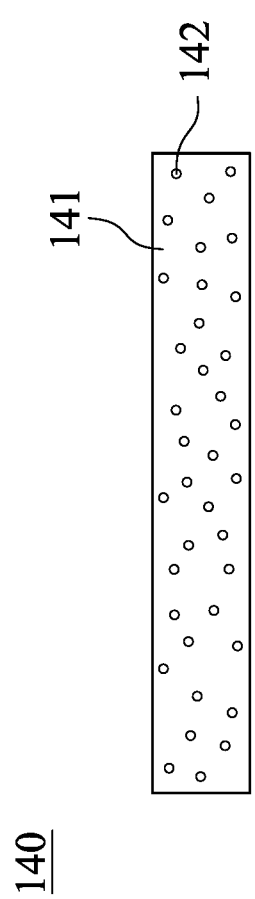
FIG. 1 is a schematic cross-sectional view illustrating an emitting layer of an OLED according to one embodiment of the present disclosure.

FIG. 1 is a schematic cross-sectional view illustrating an emitting layer 140 of an OLED according to one embodiment of the present disclosure. In FIG. 1, the emitting layer 140 includes a host material 141 and a dopant 142, wherein the dopant 142 is the aforementioned boron-containing compound (I). Thus, the OLED including the emitting layer 140 is featured with advantages of high efficiency, low cost and capable of providing a wide light color tenability. The details of the boron-containing compound (I) have been recited previously and will not be repeated herein.

A doping concentration of the dopant 142 in the emitting layer 140 can be in a range of 5% to 30%. The definition of the doping concentration is a ratio of a deposition rate of the dopant 142 to a deposition rate of the host material 141. For one example, when the ratio of the deposition rate of the dopant 142 to the deposition rate of the host material 141 is one twentieth (1/20), the doping concentration is 5%. For another example, when the ratio of the deposition rate of the dopant 142 to the deposition rate of the host material 141 is three tenths (3/10), the doping concentration is 30%.

By doping the dopant 142 in the emitting layer 140, the energy of the host material 141 can be transferred to the dopant 142, so that the light color and the luminous efficiency of the host material 141 can be changed, which can broaden the application of the OLED.

The host material 141 can be a high triplet energy host material, a hole transport type host material, an electron transport type host material or a bi-polar type host material. Specifically, the proper host material 141 can be decided according to actual demands. For example, the proper host material 141 can be decided according to the desired light color of the OLED. The host material 141 can include any one of structures of Formula (1) to Formula (9):

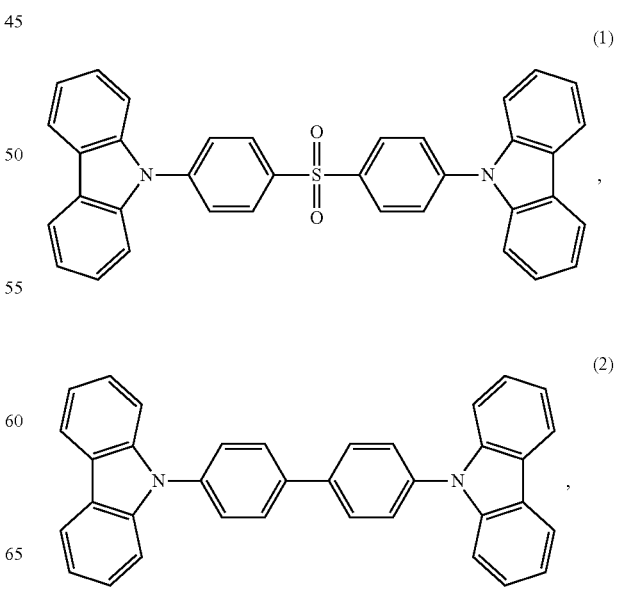

(3)
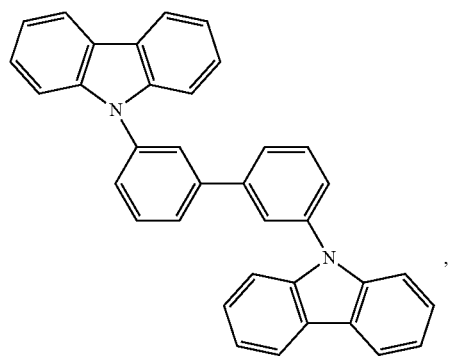

(4)
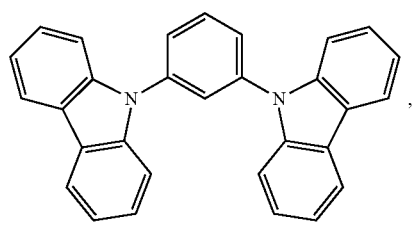

(5)
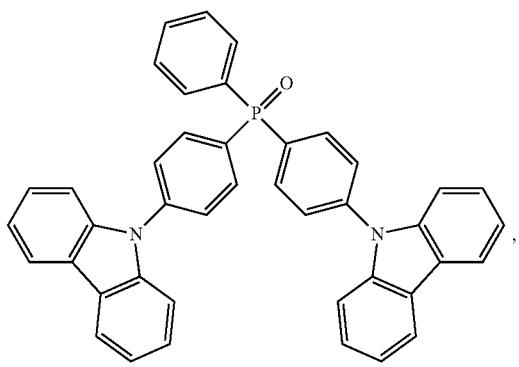

(6)
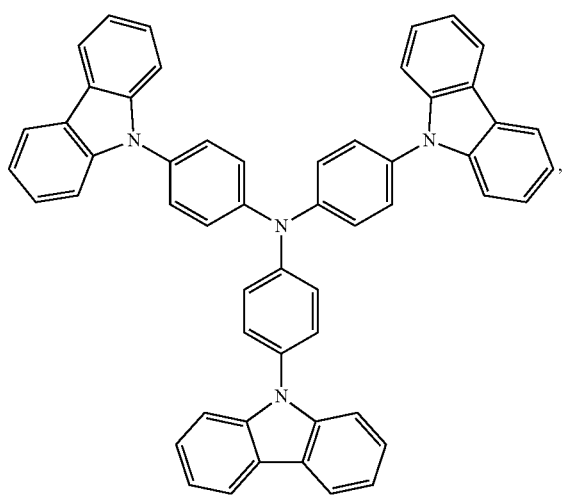

(7)
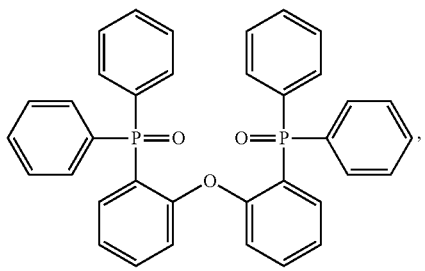

(8)
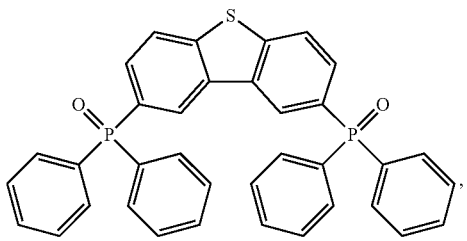

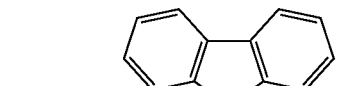

(9)
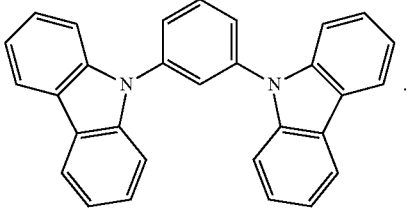

The compound name of Formula (1) is 9,9'-(sulfonylbis (4,1-phenylene))bis(9H-carbazole), and the abbreviation thereof is CzPS. The compound name of Formula (2) is 4,4'-di(9H-carbazol-9-yl)-1,1'-biphenyl, and the abbreviation thereof is CBP. The compound name of Formula (3) is 3,3'-di(9H-carbazol-9-yl)-1,1'-biphenyl, and the abbreviation thereof is mCBP. The compound name of Formula (4) is 1,3-di(9H-carbazol-9-yl)benzene, and the abbreviation thereof is mCP. The compound name of Formula (5) is bis(4-(9H-carbazol-9-yl)phenyl)(phenyl)phosphine oxide, and the abbreviation thereof is BCPO. The compound name of Formula (6) is tris(4-(9H-carbazol-9-yl)phenyl)amine, and the abbreviation thereof is TCTA. The compound name of Formula (7) is oxybis(2,1-phenylene))bis(diphenylphosphine oxide, and the abbreviation thereof is DPEPO. The compound name of Formula (8) is dibenzo[b,d]thiophene-2,8-diylbis(diphenylphosphine oxide, and the abbreviation thereof is PPT. The compound name of Formula (9) is 1,3,5-tri(9H-carbazol-9-yl)benzene, and the abbreviation thereof is TCB. The compounds of Formula (1) and (3)-(9) can be used to manufacture blue, green or red OLEDs. The compound of Formula (2) can be used to manufacture green or red OLEDs.

OLED Device

An OLED device includes the aforementioned emitting layer of the OLED. Thus, the OLED device including the emitting layer is featured with advantages of high efficiency, low cost and capable of providing a wide light color tenability.

Figure 2:
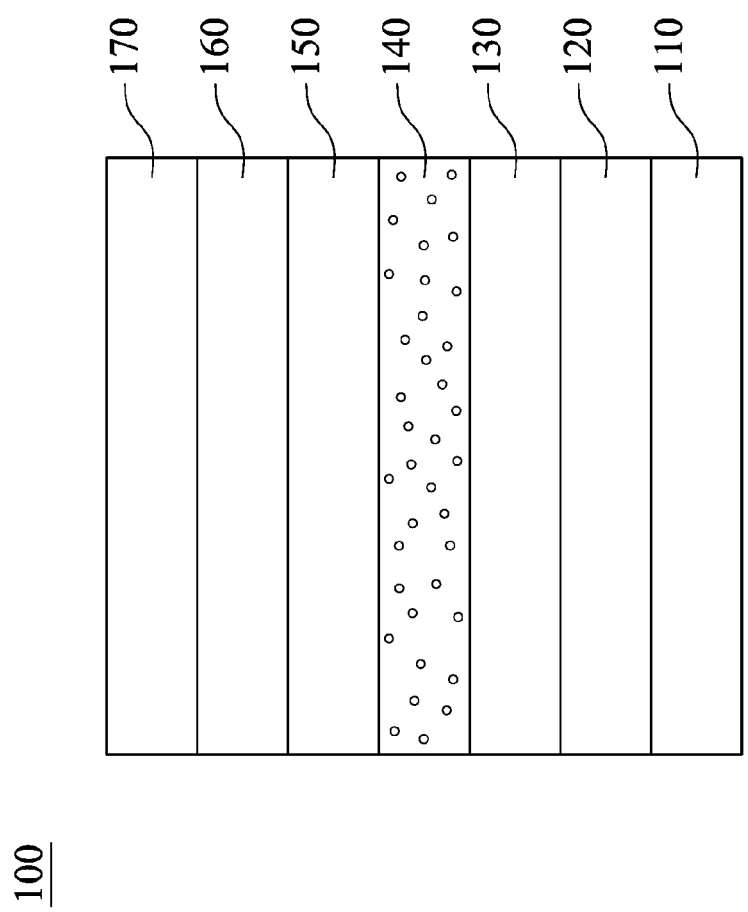
FIG. 2 is a schematic cross-sectional view illustrating an OLED device according to another embodiment of the present disclosure.

FIG. 2 is a schematic cross-sectional view illustrating an OLED device 100 according to another embodiment of the present disclosure. In FIG. 2, the OLED device 100 includes an anode 110, a hole injection layer 120, a hole-transporting layer 130, an emitting layer 140, an electron-transporting layer 150, an electron injection layer 160, and a cathode 170. The details of the emitting layer 140 have been recited previously and will not be repeated herein.

Specifically, the anode 110 can be a transparent conductive metal oxide or metal. The transparent conductive metal oxide can be ITO ($SnO_2:In_2O_3$), ZnO or AZO (Al:ZnO). The metal can be Ni, Au or Pt. When the anode 110 is the metal, a thickness of the anode 110 is preferably less than 15 nm.

The selection of the hole injection layer 120 is in consideration of the HOMO energy level thereof. Preferably, the HOMO energy level can increase the transport of the holes between the anode 110 and the hole-transporting layer 130. The hole injection layer 120 can be but is not limited to HATCN (the compound name thereof is 2,3,6,7,10,11-hexacyano-1,4,5,8,9,12-hexaazatriphenylene), $MoO_3$, NPB (the compound name thereof is 4,4'-bis(N-(1-naphthyl)-N-phenylamino)biphenyl) or NPNPB (the compound name thereof is N,N'-di-phenyl-N,N'-di-(4-(N,N-di-phenyl-amino)pheny)benzidine).

The hole-transporting layer 130 can be but is not limited to NPB or TCTA.

The electron-transporting layer 150 can be but is not limited to TPBI (the compound name thereof is 1,3,5-tris(1-phenyl-1H-benzimidazol-2-yl)benzene), TmPyPb (the compound name thereof is 3,3'-[5'-[3-(3-pyridinyl)phenyl][1,1':3',1''-terphenyl]-3,3''-diyl]bispyridine), BCP (the compound name thereof is bathocuproine), BAlq (the compound name thereof is bis(2-methyl-8-quinolinolato-N1,O8)-(1,1'-biphenyl-4-olato)aluminum), TAZ (the compound name thereof is 3-(biphenyl-4-yl)-5-(4-tert-butylphenyl)-4-phenyl-4H-1,2,4-triazole).

The electron injection layer 160 can be but is not limited to LiF.

The cathode 170 can be but is not limited to a mixture of Mg and Ag, a mixture of LiF and Al, or Al.

The OLED device 100 can further include a substrate (not shown). The OLED device 100 can be manufactured by sequentially depositing the anode 110, the hole injection layer 120, the hole-transporting layer 130, the emitting layer 140, the electron-transporting layer 150, the electron injection layer 160, and the cathode 170 on the substrate. The substrate can be a transparent glass substrate or a plastic substrate.

Synthesis of Examples

EX1: the boron-containing compound of EX1 has a structure of Formula (I-1-1):

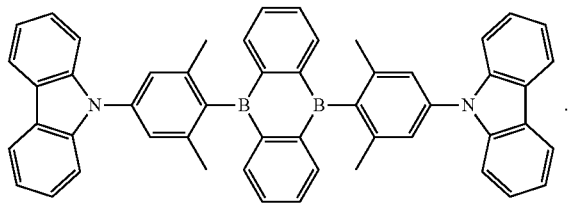

(I-1-1)

The boron-containing compound (I-1-1) of EX1 can be synthesized as follows: a solution of nBuLi in hexane, a solution of 9-(4-bromo-3,5-dimethylphenyl)-9H-carbazole in $Et_2O$ and a solution of 9,10-dibromo-9,10-diboraanthracene in toluene are prepared, respectively. The solution of nBuLi in hexane (2.5M) is prepared by dissolving nBuLi (2.5 mmol) into hexane (1.0 mL). The solution of 9-(4-bromo-3,5-dimethylphenyl)-9H-carbazole in $Et_2O$ is prepared by dissolving 9-(4-bromo-3,5-dimethylphenyl)-9H-carbazole (567 mg, 1.62 mmoL) into $Et_2O$ (40 mL). The solution of 9,10-dibromo-9,10-diboraanthracene in toluene is prepared by dissolving 9,10-dibromo-9,10-diboraanthracene (270 mg, 0.809 mmol) into toluene (25 mL).

Figure 3A:
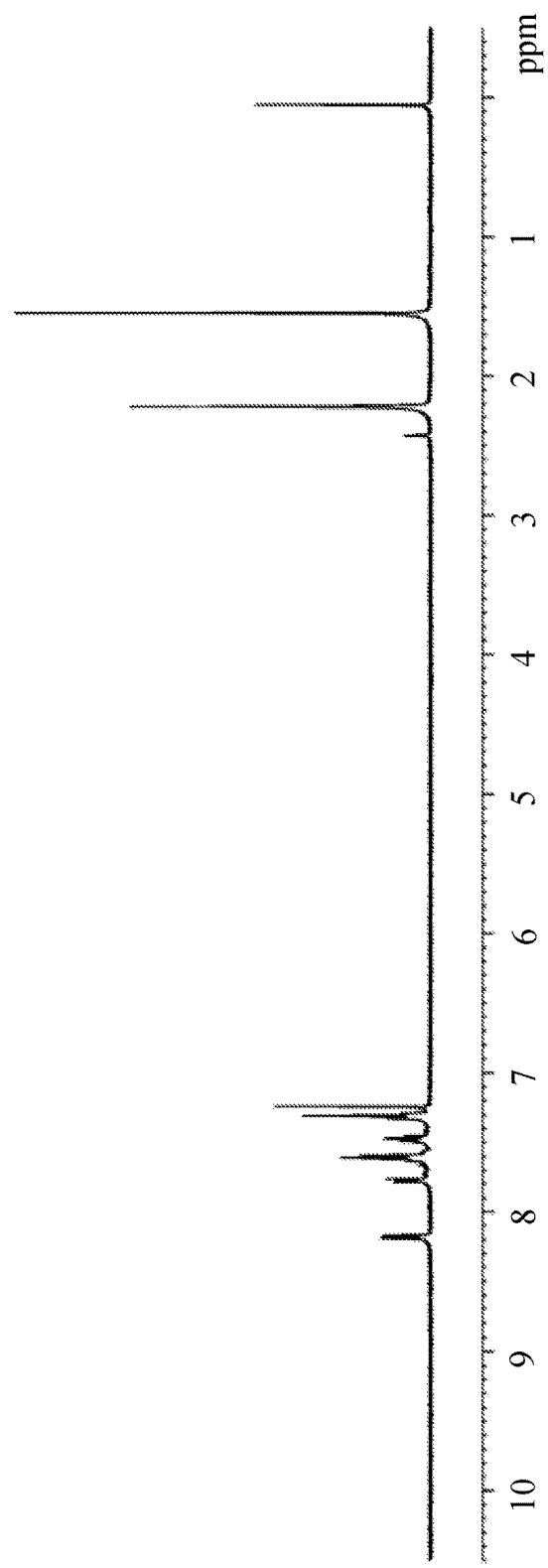
FIG. 3A is a ¹H NMR spectrum of Example 1 (EX1)
Figure 3B:
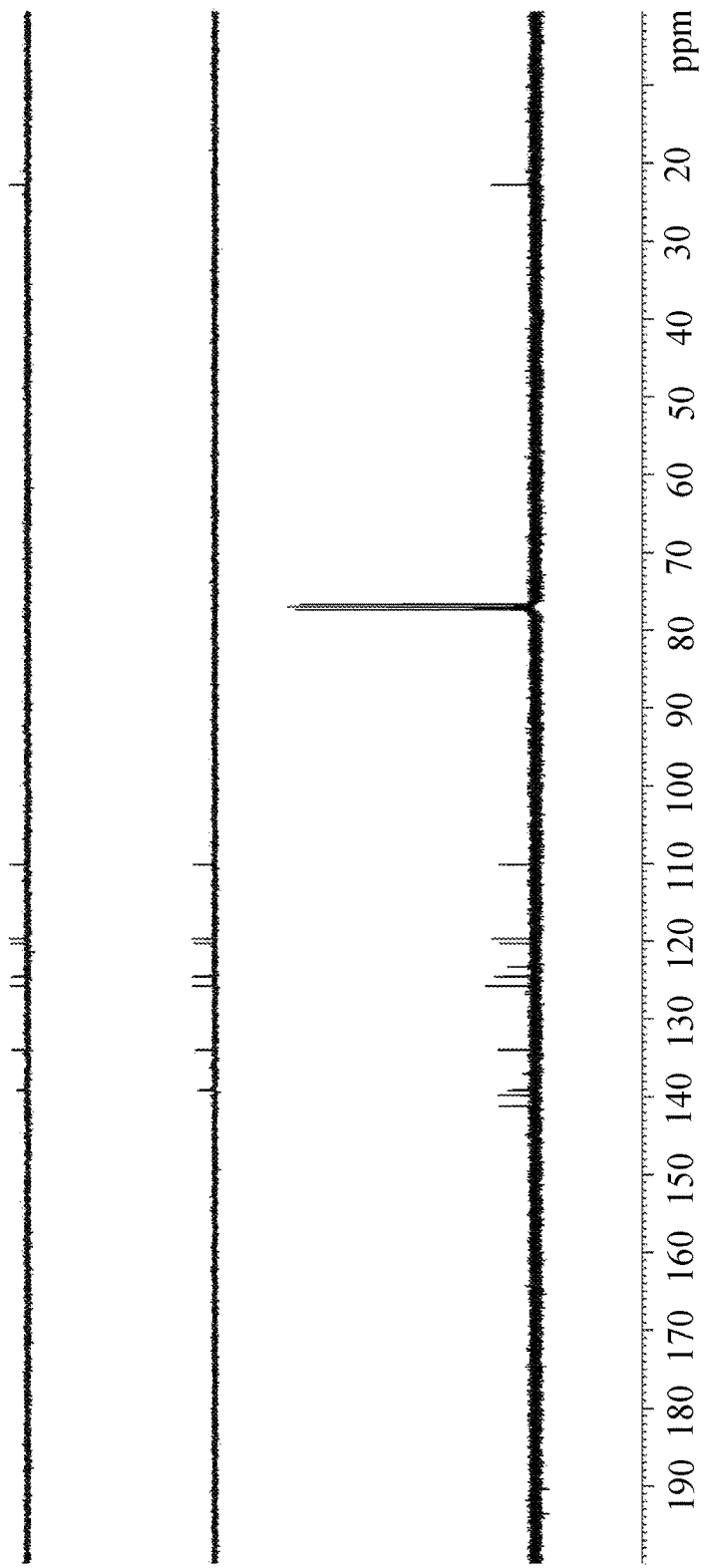
FIG. 3B is a ¹³C NMR spectrum of EX1.
Figure 3C:
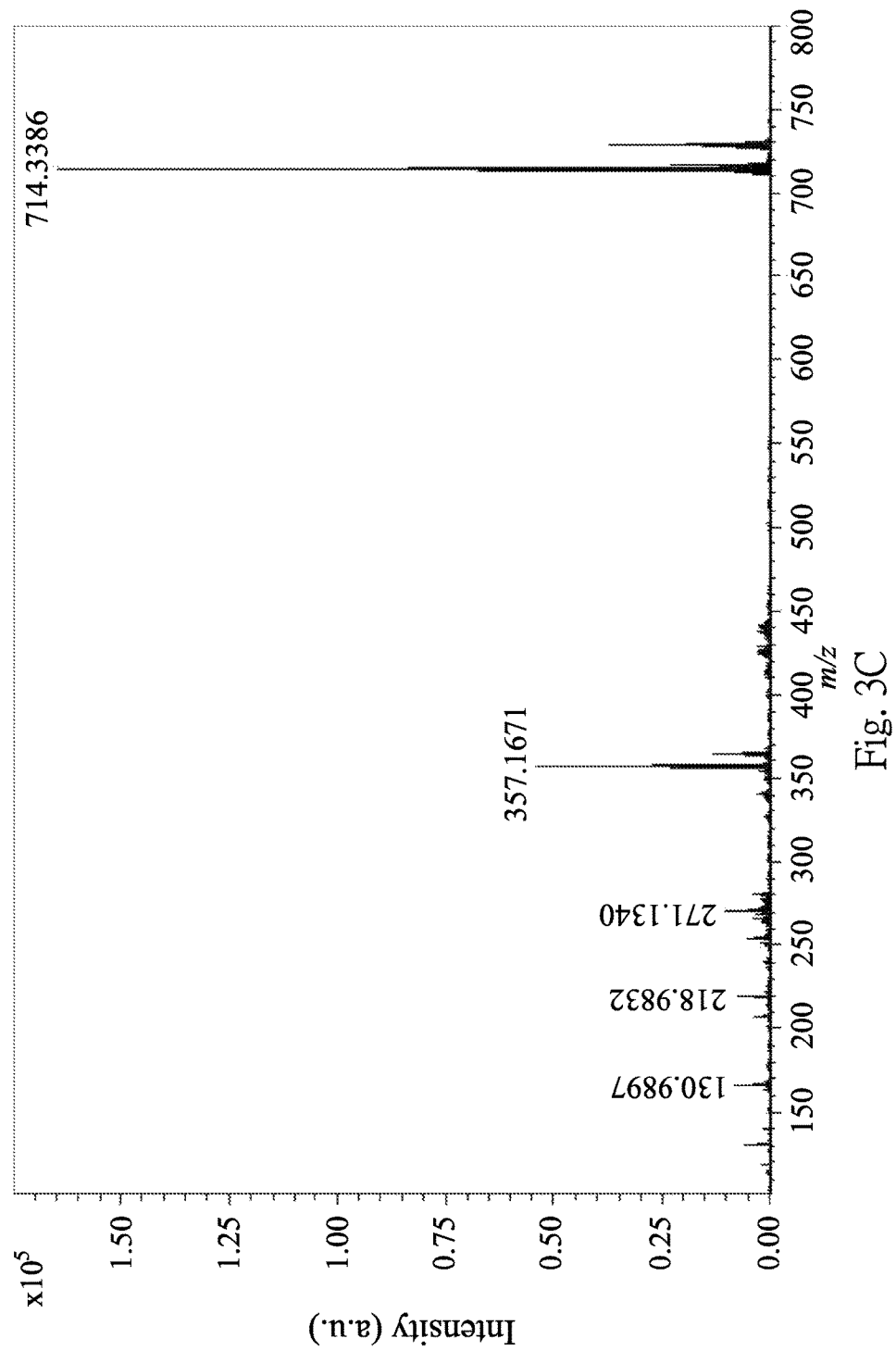
FIG. 3C is a high resolution mass spectrometry (HRMS) result of EX1.

The solution of nBuLi in hexane is added dropwise with stirring at −78° C. to the solution of 9-(4-bromo-3,5-dimethylphenyl)-9H-carbazole in $Et_2O$ so as to form a reaction mixture. Stirring is continued for 10 minutes before the reaction mixture is warmed to 0° C. within 30 minutes. The reaction mixture is cooled to −78° C. again. The solution of 9,10-dibromo-9,10-diboraanthracene in toluene is added dropwise with stirring to the reaction mixture. Afterwards, the reaction mixture is allowed to warm to room temperature overnight (about 8 hours), and all volatiles are removed under reduced pressure so as to obtain a crude product. The crude product is washed with $NH_4Cl_{(aq)}$ (30 mL) and dichloromethane (30 mL) and further purified by flash column chromatography (silica gel, hexane/dichloromethane=10:1) to obtain a product as a yellow solid (439 mg, 76%). FIG. 3A is a $^1H$ NMR spectrum of EX1. FIG. 3B is a $^{13}C$ NMR spectrum of EX1. FIG. 3C is a HRMS result of EX1. According to the measuring results of $^1H$ NMR, $^{13}C$ NMR and HRMS, it can confirm that the product of EX1 is the boron-containing compound with the structure of Formula (I-1-1). $^1H$ NMR (400 MHz, $CDCl_3$): δ 8.18 (d, J=7.6 Hz, 4H), 7.77 (dd, J=3.6, 5.2 Hz, 4H), 7.63-7.59 (m, 8H), 7.49-7.45 (m, 4H), 7.33-7.29 (m, 4H), 2.22 (s, 12H); $^{13}C$ NMR (100 MHz, $CDCl_3$): 5141.1, 139.7, 139.0, 134.0, 125.8, 124.5, 124.5, 123.3, 120.3, 119.7, 110.1, 22.8; HRMS Calcd for $C_{52}H_{40}B_2N_2$: 714.3378. Found: 714.3386.

EX2: the boron-containing compound of EX2 has a structure of Formula (I-1-2):

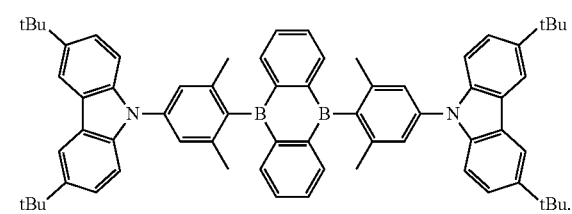

(I-1-2)

The boron-containing compound (I-1-2) of EX2 can be synthesized as follows: a solution of nBuLi in hexane, a solution of 9-(4-bromo-3,5-dimethylphenyl)-3,6-di-tert-butyl-9H-carbazole in $Et_2O$ and a solution of 9,10-dibromo-9,10-diboraanthracene in toluene are prepared, respectively. The solution of nBuLi in hexane (2.5M) is prepared by dissolving nBuLi (3.30 mmol) into hexane (1.32 mL). The solution of 9-(4-bromo-3,5-dimethylphenyl)-3,6-di-tert-butyl-9H-carbazole in $Et_2O$ is prepared by dissolving 9-(4-bromo-3,5-dimethylphenyl)-3,6-di-tert-butyl-9H-carbazole (1.02 g, 2.20 mmoL) into $Et_2O$ (40 mL). The solution of 9,10-dibromo-9,10-diboraanthracene in toluene is prepared by dissolving 9,10-dibromo-9,10-diboraanthracene (367 mg, 1.10 mmol) into toluene (25 mL).

Figure 4A:
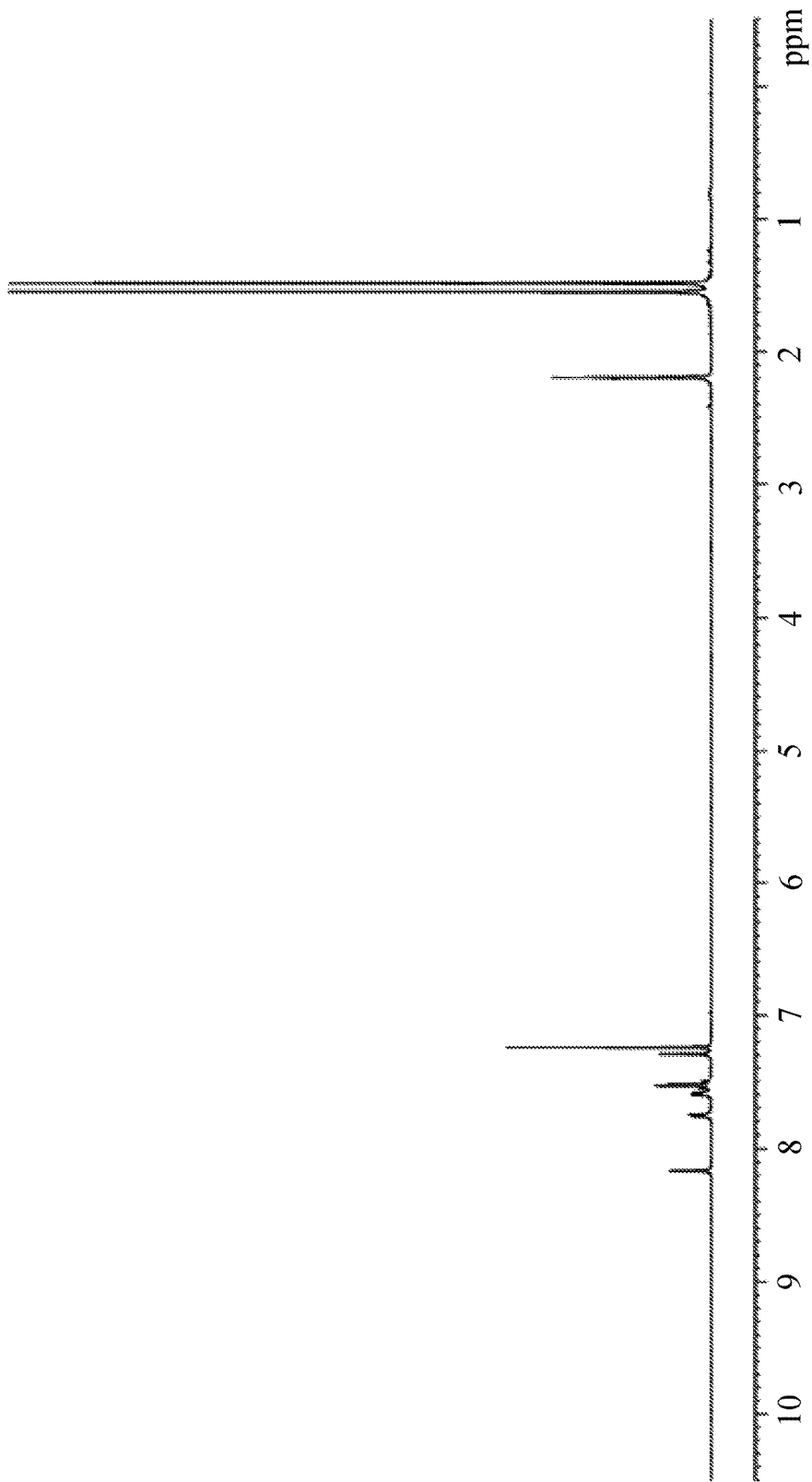
FIG. 4A is a ¹H NMR spectrum of Example 2 (EX2)
Figure 4B:
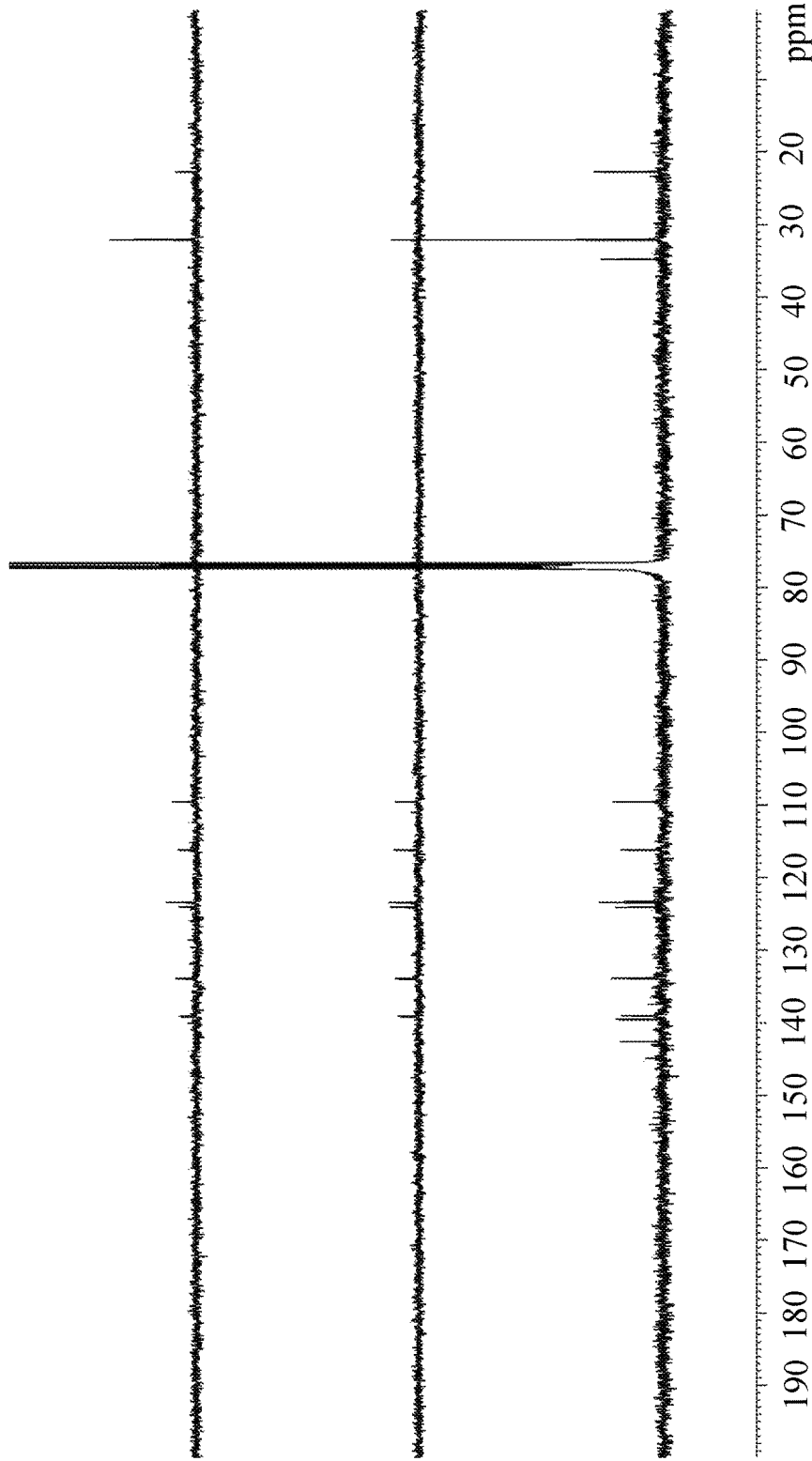
FIG. 4B is a ¹³C NMR spectrum of EX2.
Figure 4C:
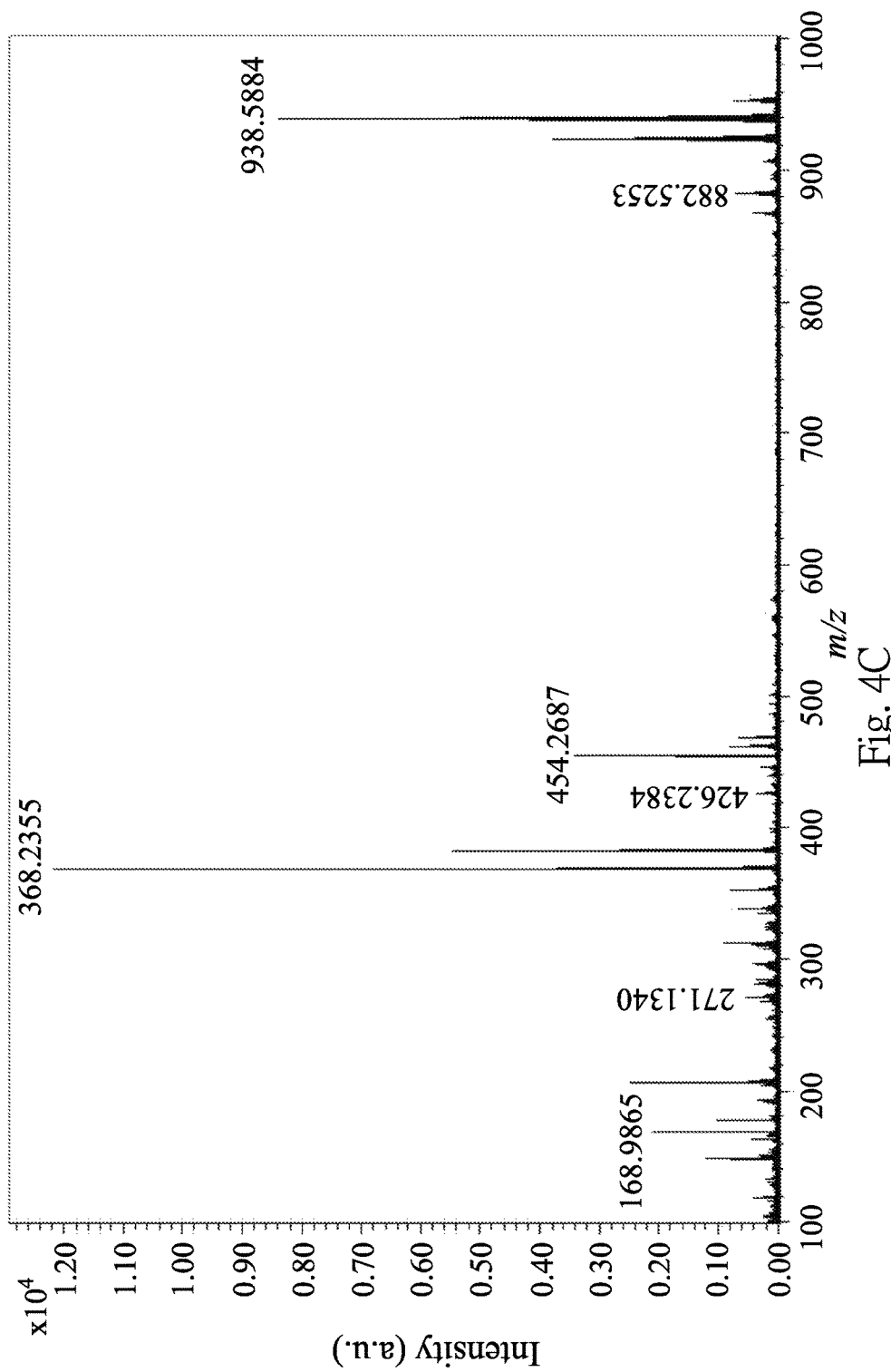
FIG. 4C is a HRMS result of EX2.

The solution of nBuLi in hexane is added dropwise with stirring at −78° C. to the solution of 9-(4-bromo-3,5-dimethylphenyl)-3,6-di-tert-butyl-9H-carbazole in Et$_2$O so as to form a reaction mixture. Stirring is continued for 10 minutes before the reaction mixture is warmed to 0° C. within 30 minutes. The reaction mixture is cooled to −78° C. again. The solution of 9,10-dibromo-9,10-diboraanthracene in toluene is added dropwise with stirring to the reaction mixture. Afterwards, the reaction mixture is allowed to warm to room temperature overnight (about 8 hours), and all volatiles are removed under reduced pressure so as to obtain a crude product. The crude product is washed with NH$_4$Cl$_{(aq)}$ (30 mL) and dichloromethane (30 mL) and further purified by flash column chromatography (silica gel, hexane/dichloromethane=10:1) to obtain a product as an orange solid (723 mg, 70%). FIG. 4A is a $^1$H NMR spectrum of EX2. FIG. 4B is a $^{13}$C NMR spectrum of EX2. FIG. 4C is a HRMS result of EX2. According to the measuring results of $^1$H NMR, $^{13}$C NMR and HRMS, it can confirm that the product of EX2 is the boron-containing compound with the structure of Formula (I-1-2). $^1$H NMR (400 MHz, CDCl$_3$): δ 8.16 (d, J=1.4 Hz, 4H), 7.76 (dd, J=3.2, 5.2 Hz, 4H), 7.60-7.50 (m, 12H), 7.49-7.45 (m, 4H), 7.29 (s, 4H), 2.20 (s, 12H), 1.48 (s, 36H); $^{13}$C NMR (100 MHz, CDCl$_3$): 6142.6, 139.5, 139.5, 139.5, 139.0, 133.9, 124.1, 123.4, 123.3, 116.2, 109.5, 34.7, 32.1, 22.7; HRMS Calcd for C$_{68}$H$_{72}$B$_2$N$_2$: 938.5882. Found: 938.5884.

EX3: the boron-containing compound of EX3 has a structure of Formula (I-1-3):

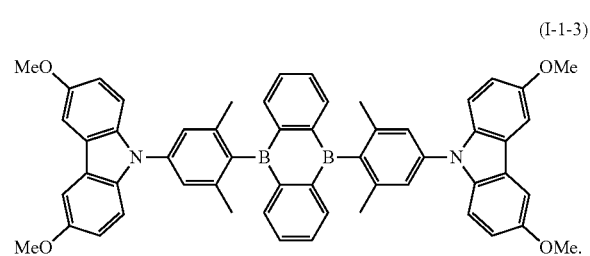 [SMILES: COc1ccc2c(c1)c1cc(OC)ccc1n2-c1cc(C)c(B2c3ccccc3B(c3c(C)cc(-n4c5ccc(OC)cc5c5cc(OC)ccc54)cc3C)c3ccccc32)c(C)c1]

(I-1-3)

The boron-containing compound (I-1-3) of EX3 can be synthesized as follows: a solution of nBuLi in hexane, a solution of 9-(4-bromo-3,5-dimethylphenyl)-3,6-dimethoxy-9H-carbazole in Et$_2$O and a solution of 9,10-dibromo-9,10-diboraanthracene in toluene are prepared, respectively. The solution of nBuLi in hexane (2.5M) is prepared by dissolving nBuLi (4.56 mmol) into hexane (1.82 mL). The solution of 9-(4-bromo-3,5-dimethylphenyl)-3,6-dimethoxy-9H-carbazole in Et$_2$O is prepared by dissolving 9-(4-bromo-3,5-dimethylphenyl)-3,6-dimethoxy-9H-carbazole (1.25 g, 3.04 mmoL) into Et$_2$O (40 mL). The solution of 9,10-dibromo-9,10-diboraanthracene in toluene is prepared by dissolving 9,10-dibromo-9,10-diboraanthracene (507 mg, 1.52 mmol) into toluene (25 mL).

Figure 5A:
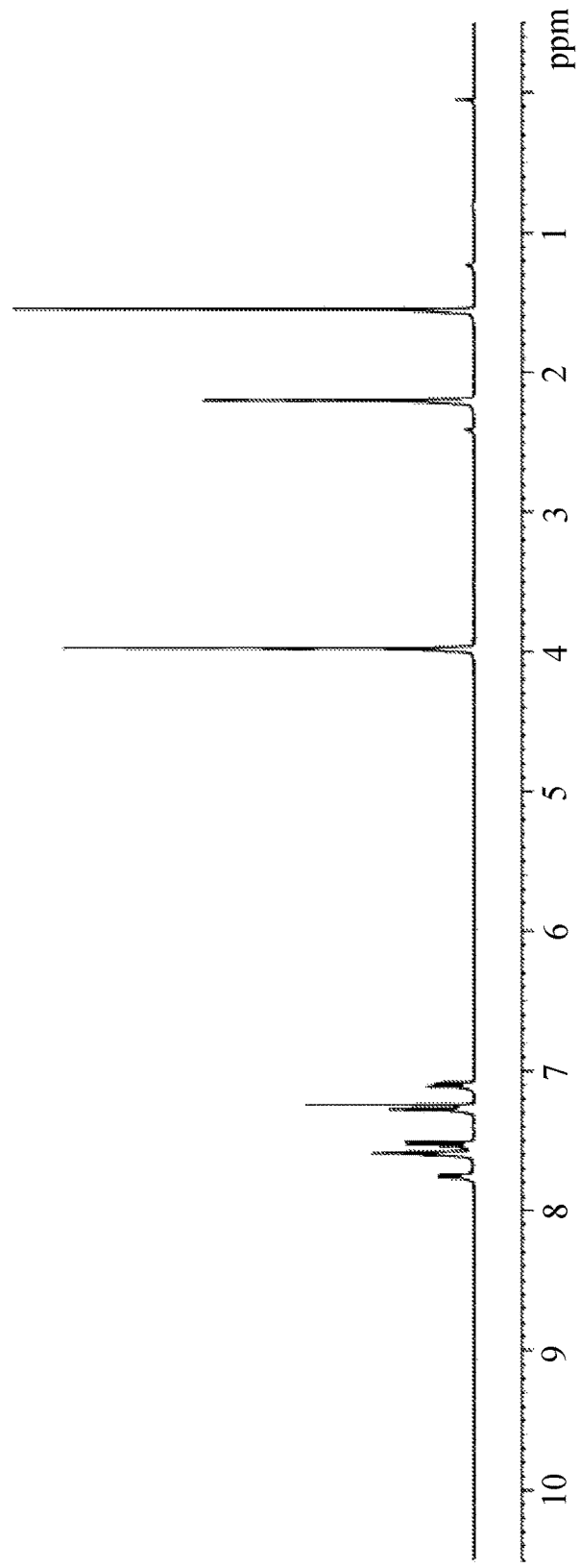
FIG. 5A is a ¹H NMR spectrum of Example 3 (EX3)
Figure 5B:
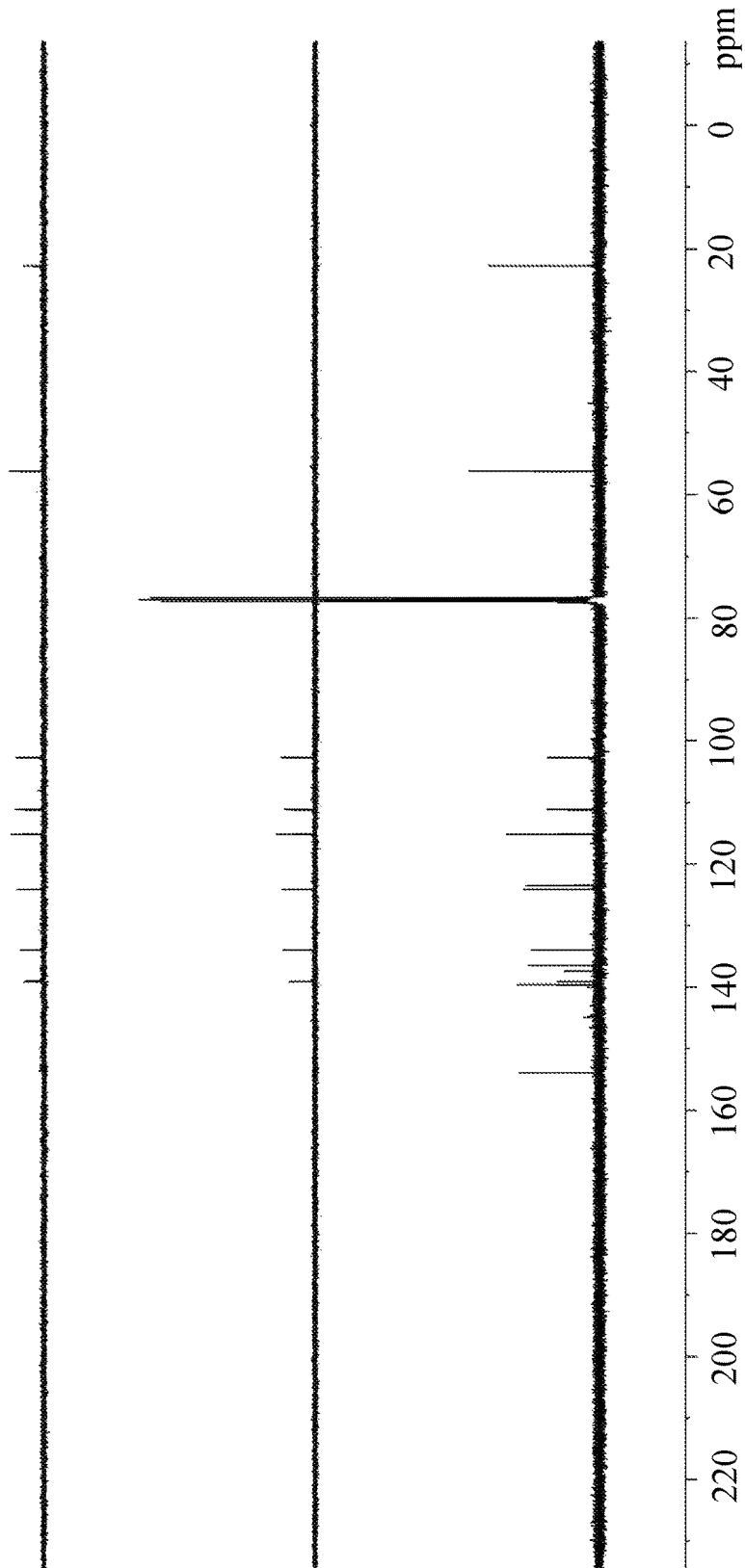
FIG. 5B is a ¹³C NMR spectrum of EX3.
Figure 5C:
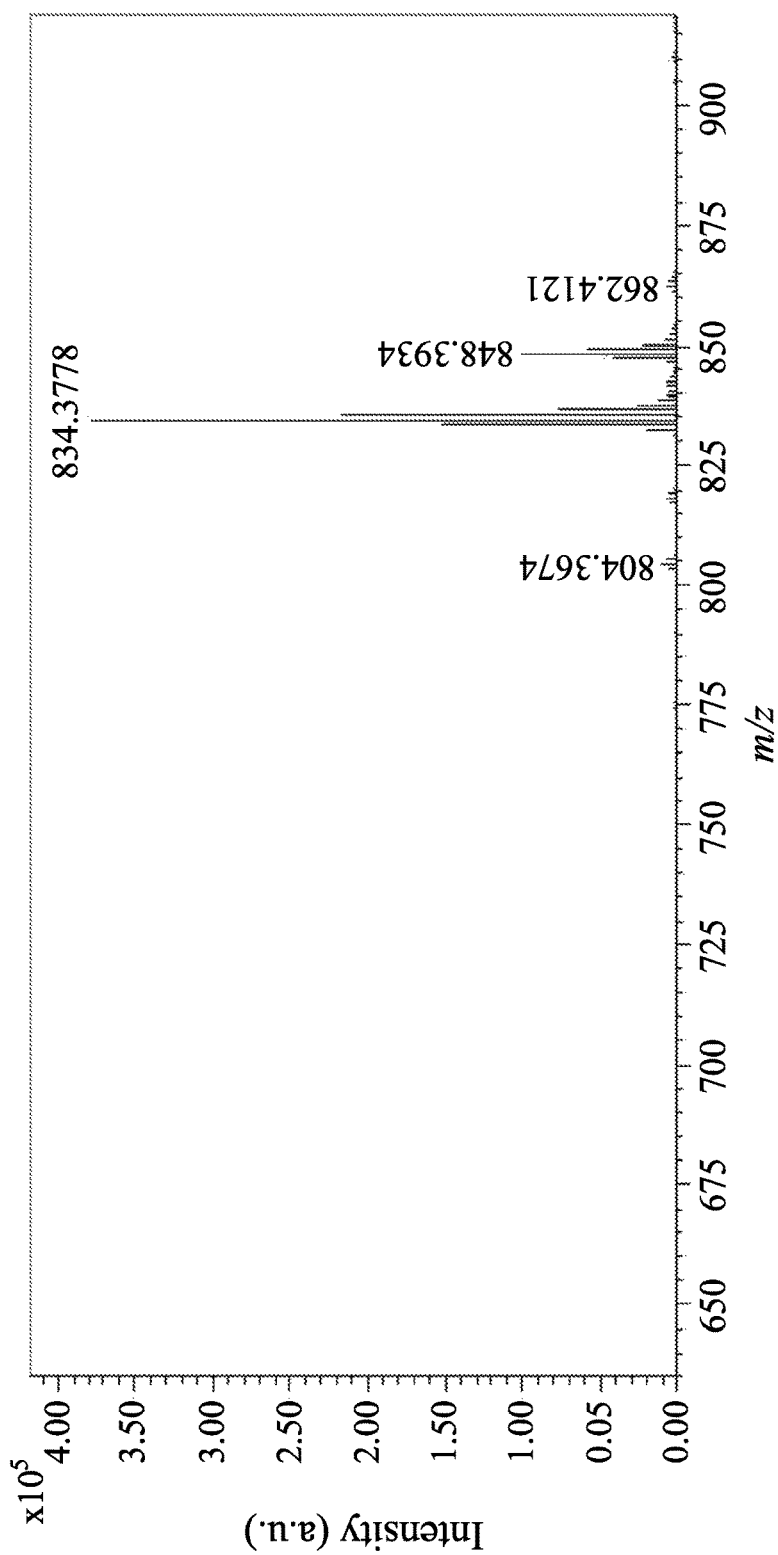
FIG. 5C is a HRMS result of EX3.

The solution of nBuLi in hexane is added dropwise with stirring at −78° C. to the solution of 9-(4-bromo-3,5-dimethylphenyl)-3,6-dimethoxy-9H-carbazole in Et$_2$O so as to form a reaction mixture. Stirring is continued for 10 minutes before the reaction mixture is warmed to 0° C. within 30 minutes. The reaction mixture is cooled to −78° C. again. The solution of 9,10-dibromo-9,10-diboraanthracene in toluene is added dropwise with stirring to the reaction mixture. Afterwards, the reaction mixture is allowed to warm to room temperature overnight (about 8 hours), and all volatiles are removed under reduced pressure so as to obtain a crude product. The crude product is washed with NH$_4$Cl$_{(aq)}$ (30 mL) and dichloromethane (30 mL) and further purified by flash column chromatography (silica gel, hexane/dichloromethane=10:1) to obtain a product as an orange solid (837 mg, 66%). FIG. 5A is a $^1$H NMR spectrum of EX3. FIG. 5B is a $^{13}$C NMR spectrum of EX3. FIG. 50C is a HRMS result of EX3. According to the measuring results of $^1$H NMR, $^{13}$C NMR and HRMS, it can confirm that the product of EX3 is the boron-containing compound with the structure of Formula (I-1-3). $^1$H NMR (400 MHz, CDCl$_3$): δ 7.75 (dd, J=3.2, 5.2 Hz, 4H), 7.60-7.58 (m, 8H), 7.52 (d, J=8.8, 4H), 7.28 (s, 4H), 7.10 (dd, J=2.4, 8.8 Hz, 4H), 3.97 (s, 12H), 2.20 (s, 12H); $^{13}$C NMR (100 MHz, CDCl$_3$): 8153.9, 139.6, 139.0, 137.4, 136.5, 133.9, 124.1, 123.5, 115.2, 111.1, 102.8, 56.2, 22.8; HRMS Calcd for C$_{56}$H$_{48}$B$_2$N$_2$O$_4$: 834.3800. Found: 834.3778.

EX4: the boron-containing compound of EX4 has a structure of Formula (I-1-4):

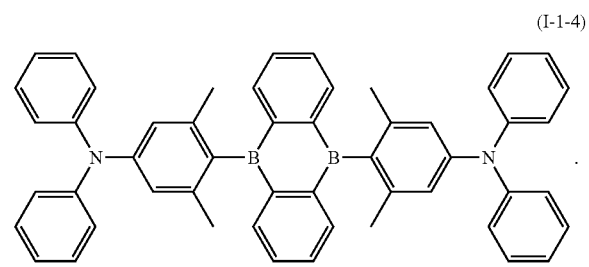 [SMILES: Cc1cc(N(c2ccccc2)c2ccccc2)cc(C)c1B1c2ccccc2B(c2c(C)cc(N(c3ccccc3)c3ccccc3)cc2C)c2ccccc21]

(I-1-4)

The boron-containing compound (I-1-4) of EX4 can be synthesized as follows: a solution of nBuLi in hexane, a solution of 4-bromo-3,5-dimethyl-N,N-diphenylaniline in Et$_2$O and a solution of 9,10-dibromo-9,10-diboraanthracene in toluene are prepared, respectively. The solution of nBuLi in hexane (2.5M) is prepared by dissolving nBuLi (3.78 mmol) into hexane (1.51 mL). The solution of 4-bromo-3,5-dimethyl-N,N-diphenylaniline in Et$_2$O is prepared by dissolving 4-bromo-3,5-dimethyl-N,N-diphenylaniline (888 mg, 2.52 mmoL) into Et$_2$O (40 mL). The solution of 9,10-dibromo-9,10-diboraanthracene in toluene is prepared by dissolving 9,10-dibromo-9,10-diboraanthracene (420 mg, 1.26 mmol) into toluene (25 mL).

Figure 6A:
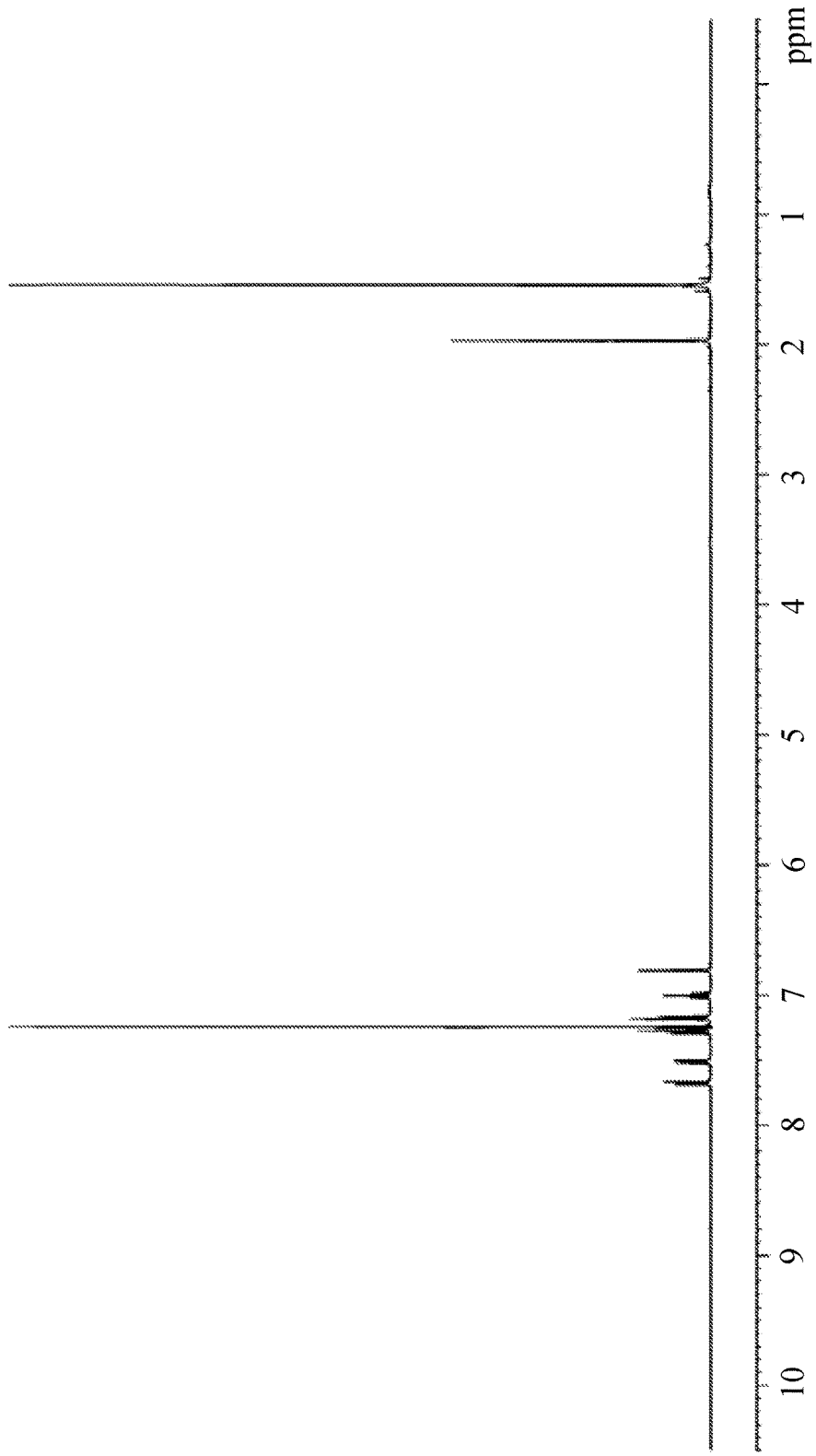
FIG. 6A is a ¹H NMR spectrum of Example 4 (EX4)
Figure 6B:
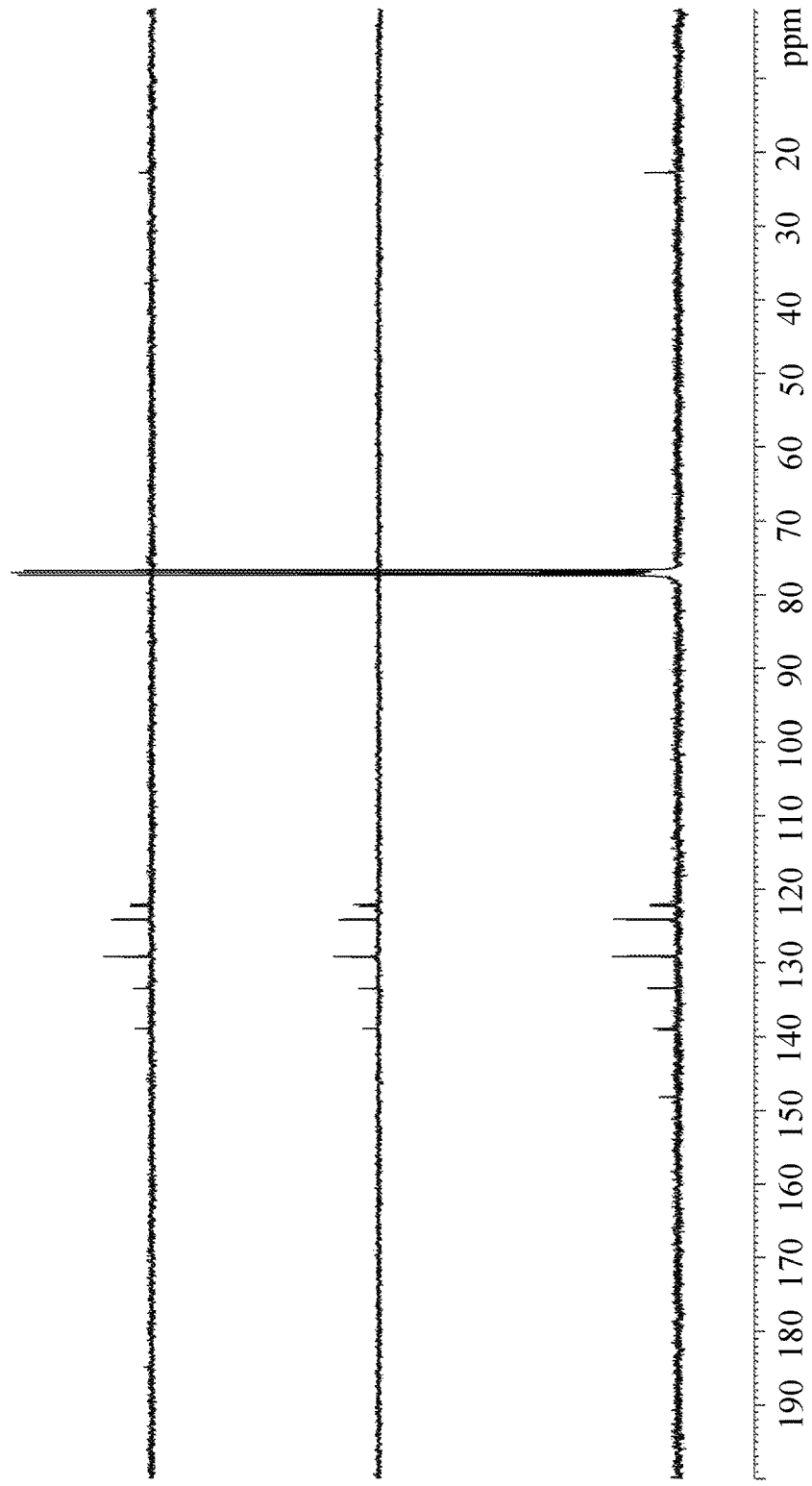
FIG. 6B is a ¹³C NMR spectrum of EX4.
Figure 6C:
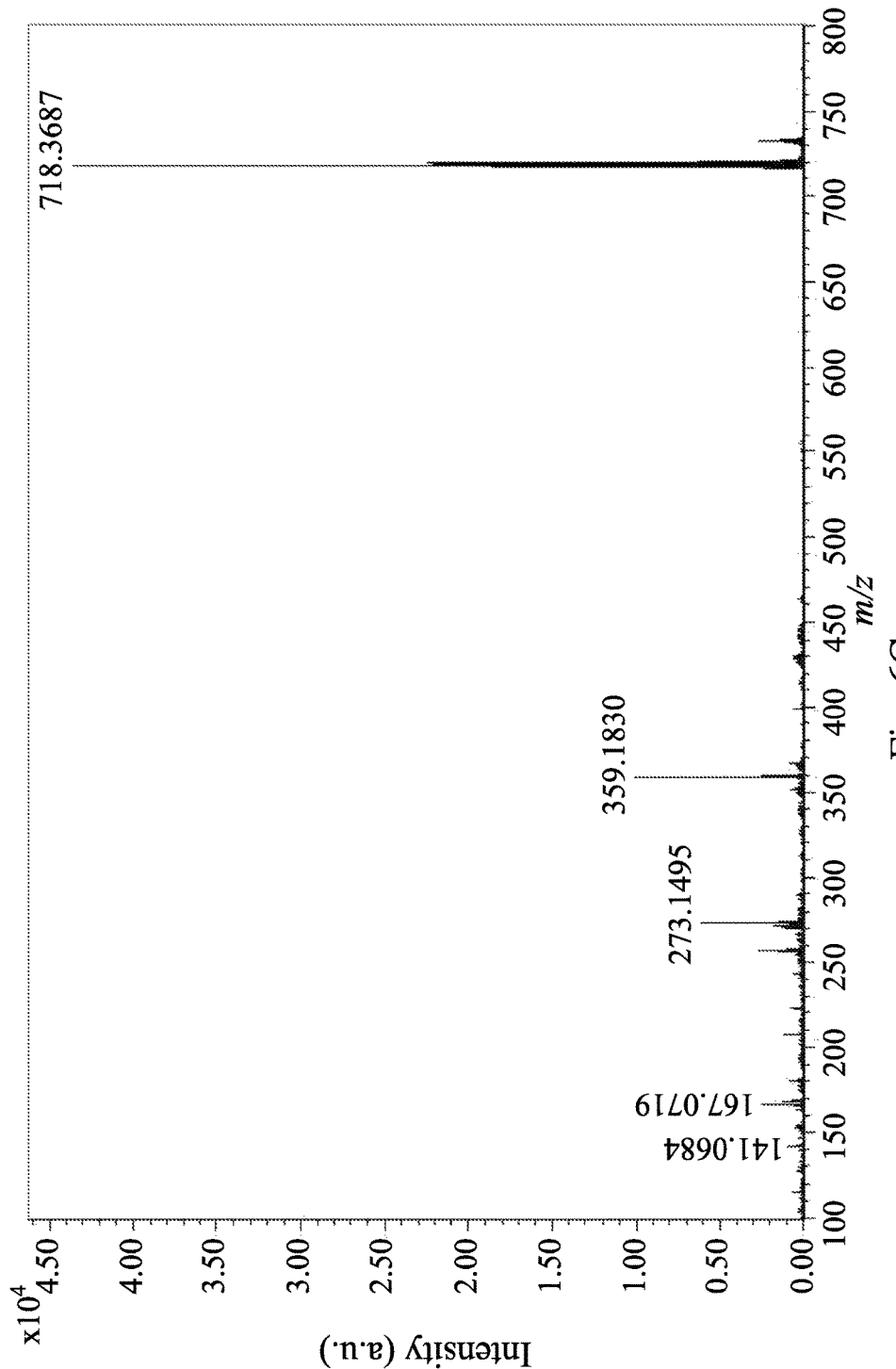
FIG. 6C is a HRMS result of EX4.

The solution of nBuLi in hexane is added dropwise with stirring at −78° C. to the solution of 4-bromo-3,5-dimethyl-N,N-diphenylaniline in Et$_2$O so as to form a reaction mixture. Stirring is continued for 10 minutes before the reaction mixture is warmed to 0° C. within 30 minutes. The reaction mixture is cooled to −78° C. again. The solution of 9,10-dibromo-9,10-diboraanthracene in toluene is added dropwise with stirring to the reaction mixture. Afterwards, the reaction mixture is allowed to warm to room temperature overnight (about 8 hours), and all volatiles are removed under reduced pressure so as to obtain a crude product. The crude product is washed with NH$_4$Cl$_{(aq)}$ (30 mL) and dichloromethane (30 mL) and further purified by flash column chromatography (silica gel, hexane/dichloromethane=10:1) to obtain a product as a red solid (534 mg, 59%). FIG. 6A is a $^1$H NMR spectrum of EX4. FIG. 6B is a $^{13}$C NMR spectrum of EX4. FIG. 6C is a HRMS result of EX4. According to the measuring results of $^1$H NMR, $^{13}$C NMR and HRMS, it can confirm that the product of EX4 is the boron-containing compound with the structure of Formula (I-1-4). $^1$H NMR (400 MHz, CDCl$_3$): 67.68 (dd, J=3.2, 5.6 Hz, 4H), 7.51 (dd, J=3.2, 5.2 Hz, 4H), 7.30-7.26 (m, 8H), 7.19-7.16 (m, 8H), 7.02-6.98 (m, 4H), 6.81 (s, 4H), 1.97 (s, 12H); $^{13}$C NMR (100 MHz, CDCl$_3$): δ 148.2, 139.0, 138.8, 133.5, 129.1, 124.1, 124.1, 122.3, 122.1, 22.7; HRMS Calcd for $Cs_2H_4B_2N_2$: 718.3691. Found: 718.3687.

Measurements of Optical Property of Examples

Figure 7A:
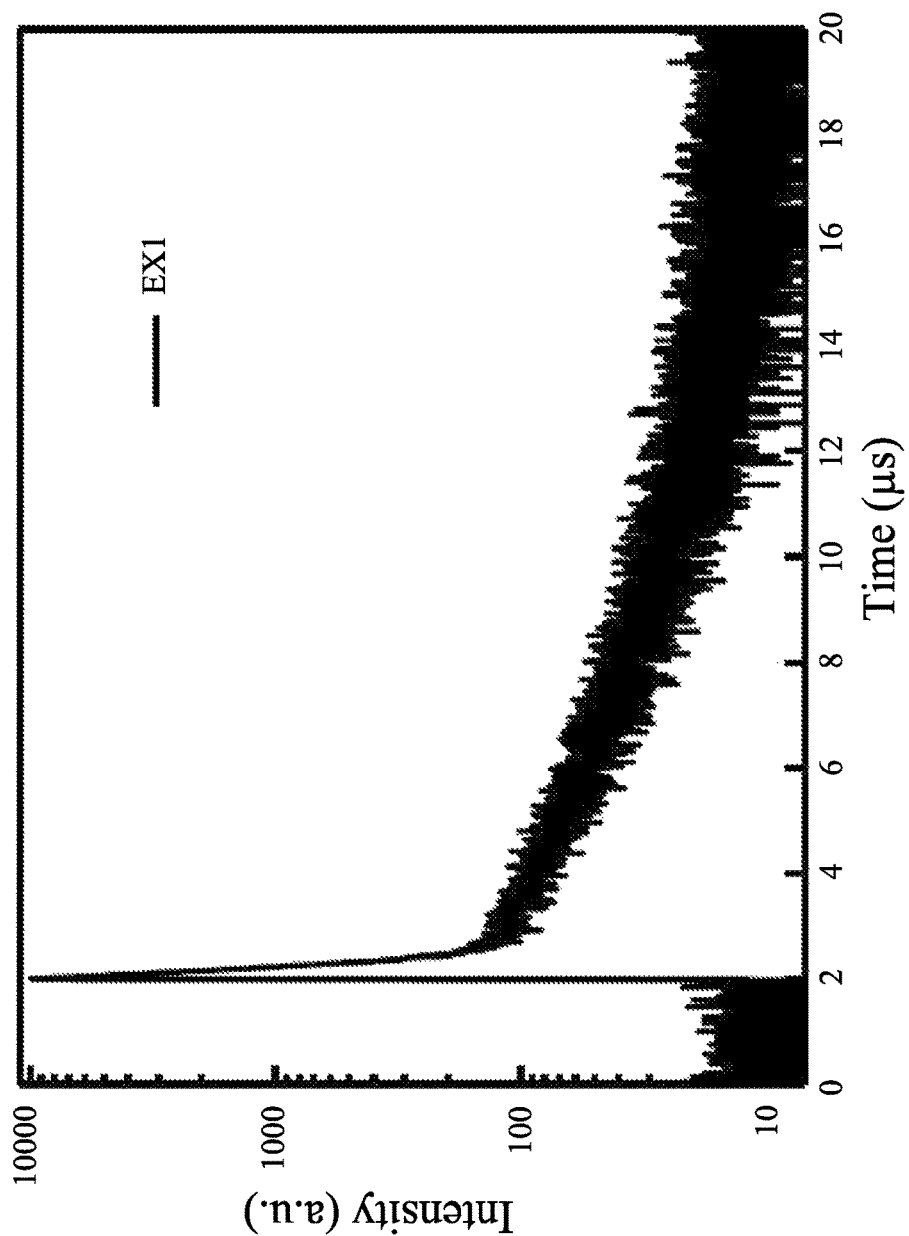
FIG. 7A is a diagram showing transient photoluminescence characteristic of EX1.
Figure 7B:
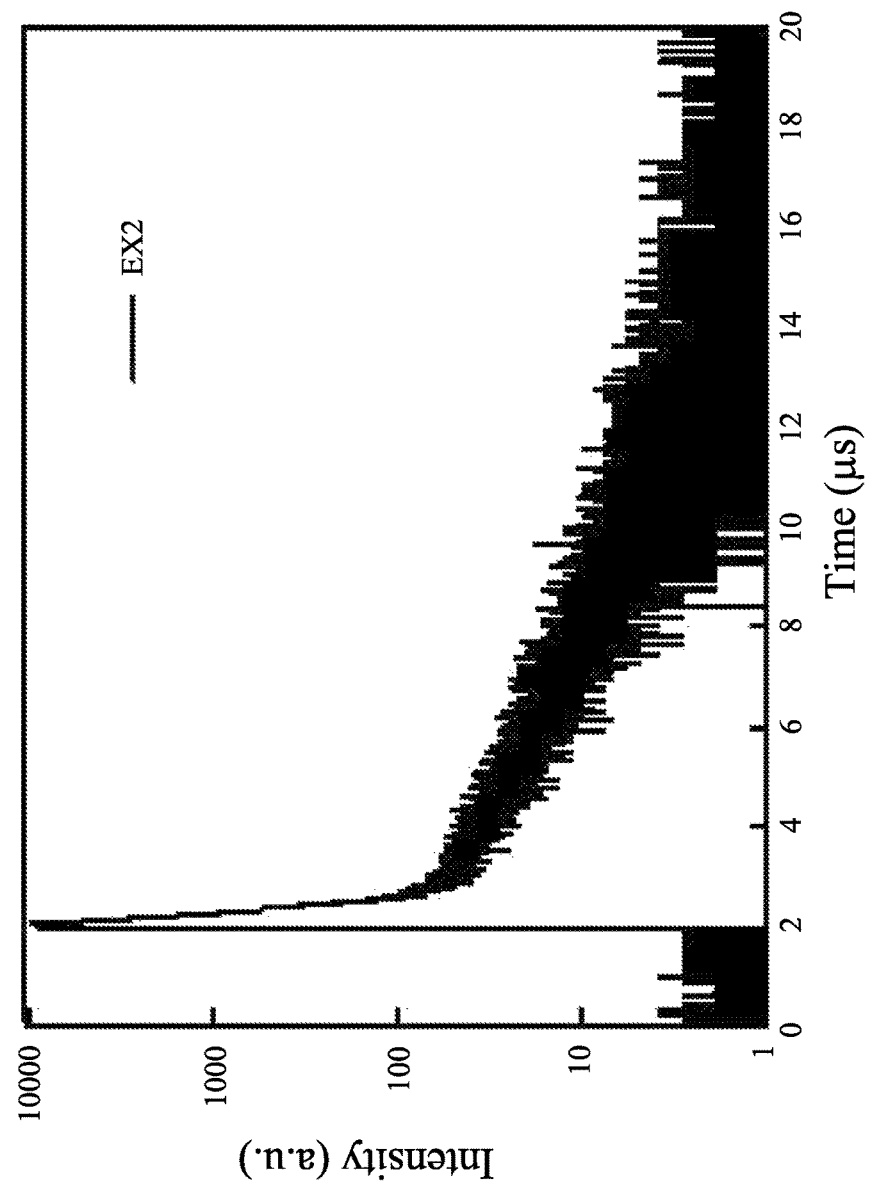
FIG. 7B is a diagram showing transient photoluminescence characteristic of EX2.
Figure 7C:
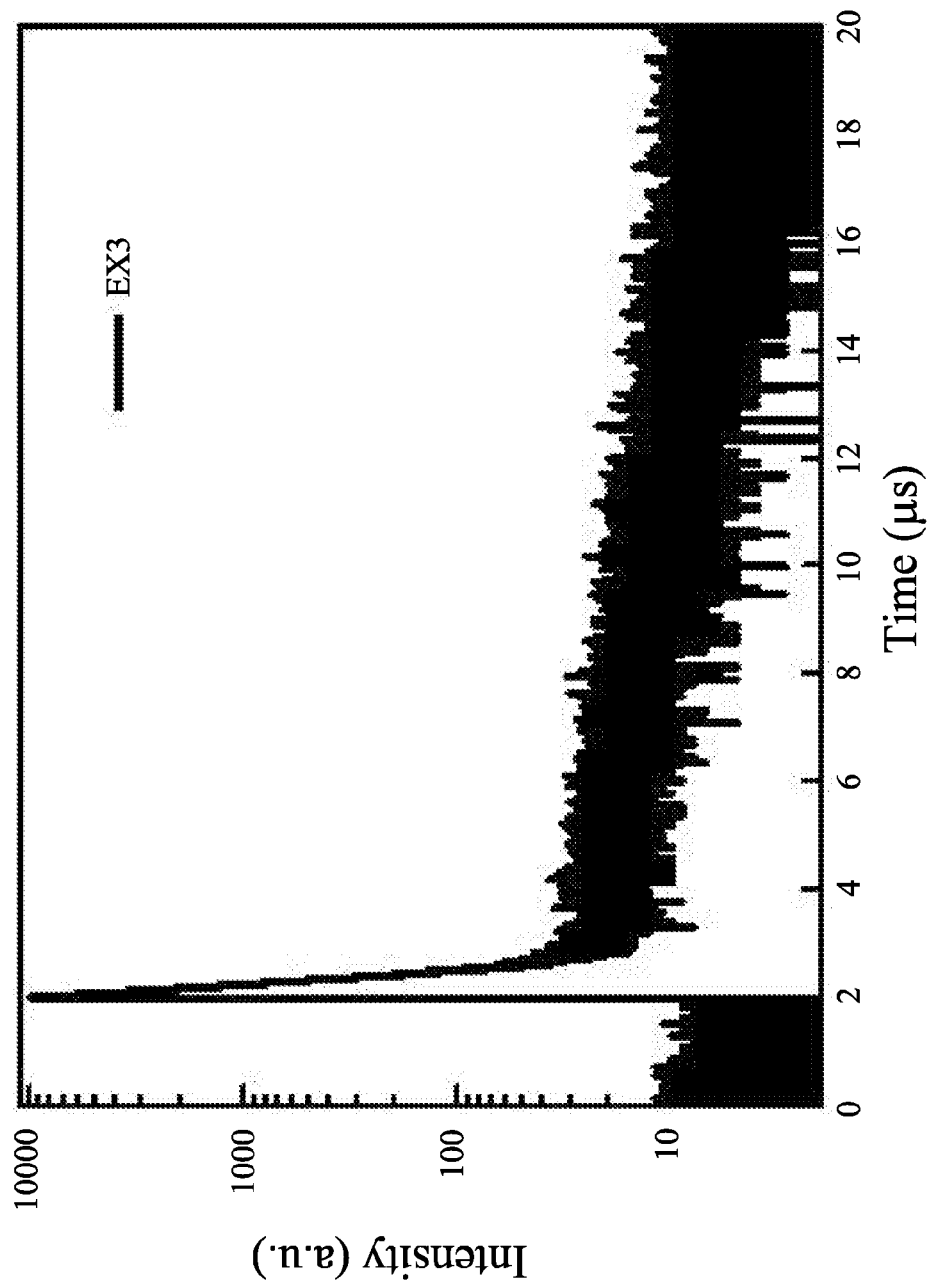
FIG. 7C is a diagram showing transient photoluminescence characteristic of EX3.
Figure 7D:
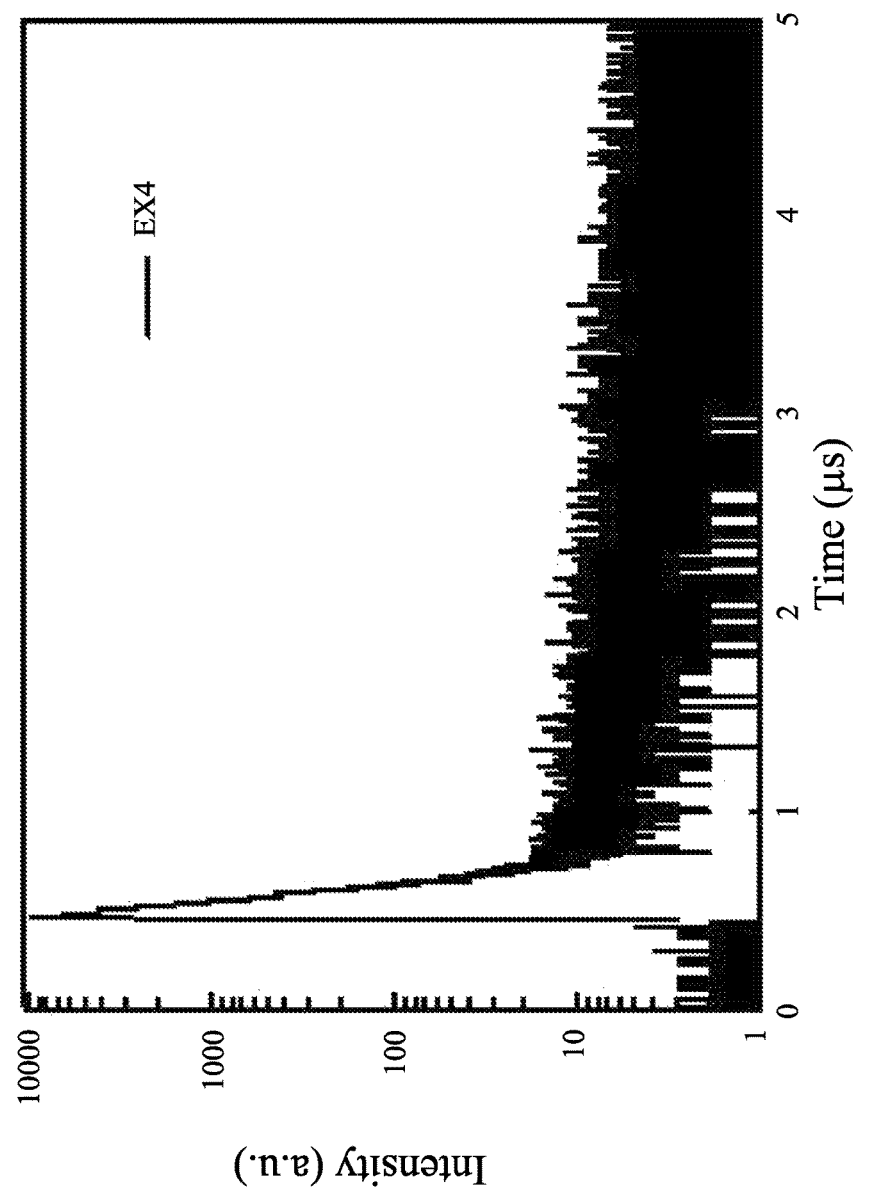
FIG. 7D is a diagram showing transient photoluminescence characteristic of EX4.

FIG. 7A is a diagram showing transient photoluminescence characteristic of EX1. FIG. 7B is a diagram showing transient photoluminescence characteristic of EX2. FIG. 7C is a diagram showing transient photoluminescence characteristic of EX3. FIG. 7D is a diagram showing transient photoluminescence characteristic of EX4. FIGS. 7A-7D are obtained by dissolving the boron-containing compounds of EX1 to EX4 in toluene to form four solutions ($10^{-5}$ M), and the four solutions are measured at 300K under vacuum, respectively. From FIG. 7A, it can be calculated that the lifetime of fluorescence (τ1) of EX1 is 91.84 ns, and the lifetime of delayed fluorescence (τ2) of EX1 is 3.66 ps. From FIG. 7B, it can be calculated that the lifetime of fluorescence of EX2 is 108.75 ns, and the lifetime of delayed fluorescence of EX2 is 2.68 ps. From FIG. 7C, it can be calculated that the lifetime of fluorescence of EX3 is 103.37 ns, and the lifetime of delayed fluorescence of EX3 is 1.15 μs. From FIG. 7D, it can be calculated that the lifetime of fluorescence of EX4 is 35.04 ns, and the lifetime of delayed fluorescence of EX4 is 1.29 μs. As shown in FIGS. 7A-7D, the boron-containing compounds of EX1 to EX4 have the TADF property.

Figure 8:
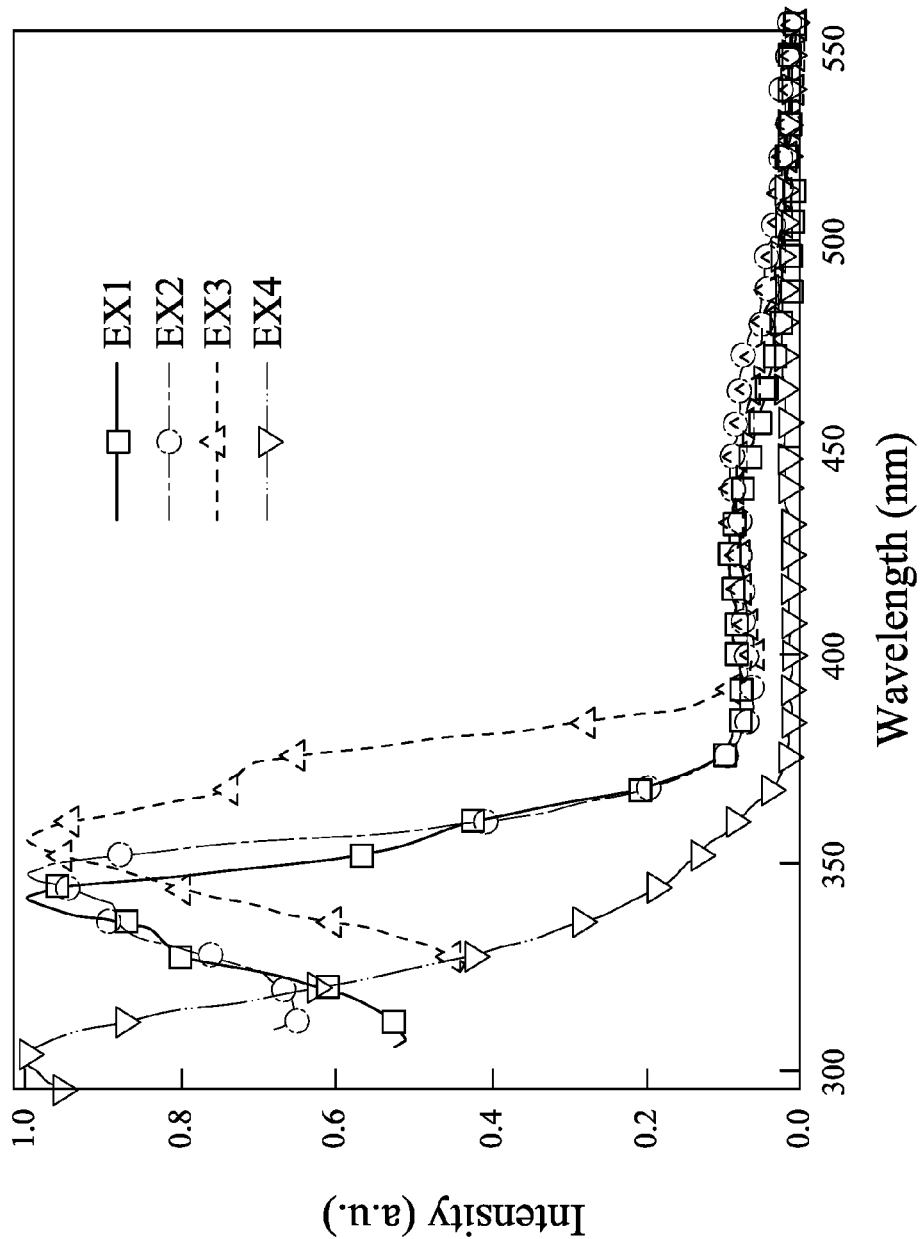
FIG. 8 shows absorption spectra of EX1 to EX4.
Figure 9:
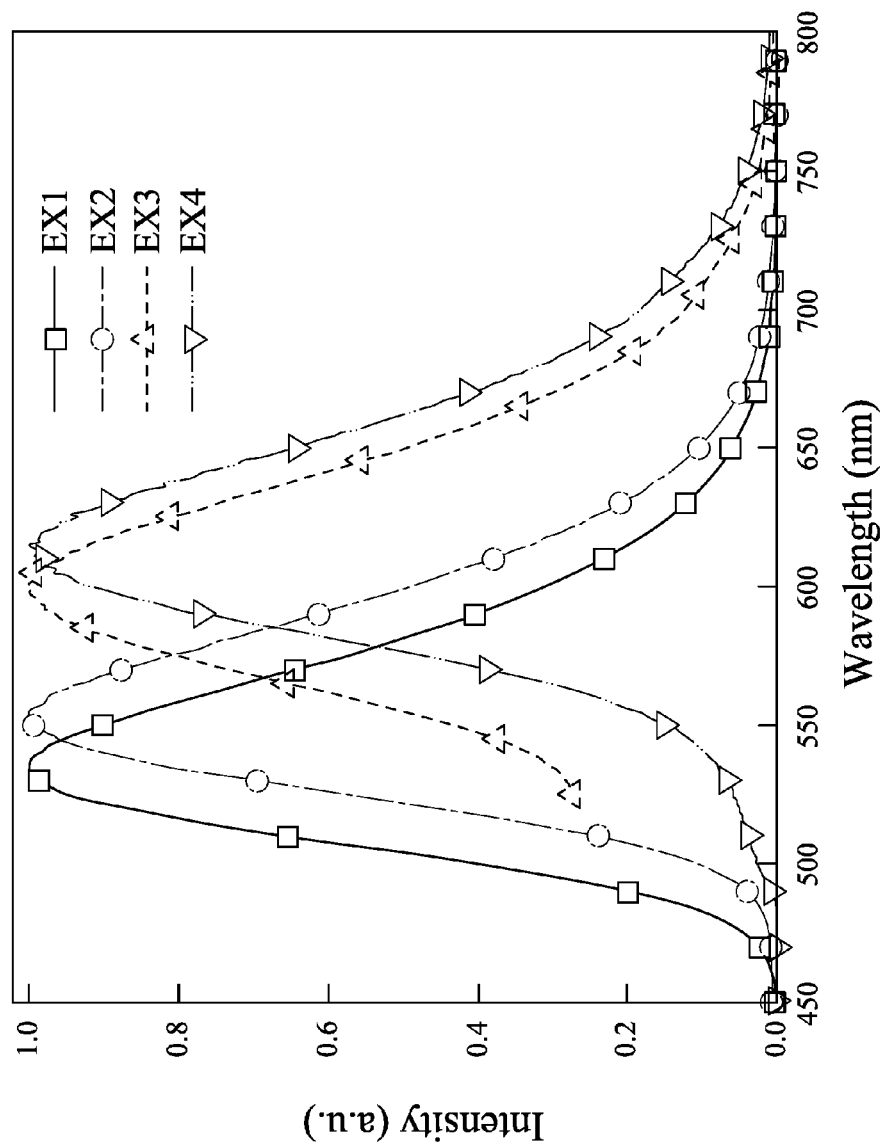
FIG. 9 shows photoluminescence spectra of EX1 to EX4.

FIG. 8 shows absorption spectra of EX1 to EX4. FIG. 9 shows photoluminescence spectra of EX1 to EX4. FIGS. 8-9 are obtained by dissolving the boron-containing compounds of EX1 to EX4 in dichloromethane to form four solutions ($10^{-5}$ M), and the four solutions are measured at 300K, respectively. The maximum absorption wavelength ($\lambda_{Absmax}$) and the maximum photoluminescence wavelength ($\lambda_{PLmax}$) of each of EX1 to EX4 can be obtained from FIGS. 8-9, and are listed in Table 1. In Table 1, $E_{HOMO}$ refers to the HOMO energy level, which is measured by a photoelectron spectrometer surface analyzer (Model AC-2). $E_{LUMO}$ refers to the LUMO energy level, which is calculated by "$E_{HOMO} - E_{band\ gap}$", wherein the $E_{band\ gap}$ is obtained by the absorption spectrum, and is calculated by "$E_{band\ gap} = 1241/\lambda_{onset}$ (nm)".

TABLE 1

| EX | $\lambda_{Absmax}$ (nm) | $\lambda_{PLmax}$ (nm) | $E_{HOMO}$ (eV) | $E_{LUMO}$ (eV) | $E_{band\ gap}$ (eV) |
|---|---|---|---|---|---|
| 1 | 342 | 533 | −5.93 | −3.23 | −2.70 |
| 2 | 348 | 554 | −5.88 | −3.14 | −2.74 |
| 3 | 356 | 601 | −5.45 | −3.20 | −2.25 |
| 4 | 304 | 613 | −5.66 | −3.56 | −2.10 |

Measurements of Air/Moisture Stability of Examples

Figure 3D:
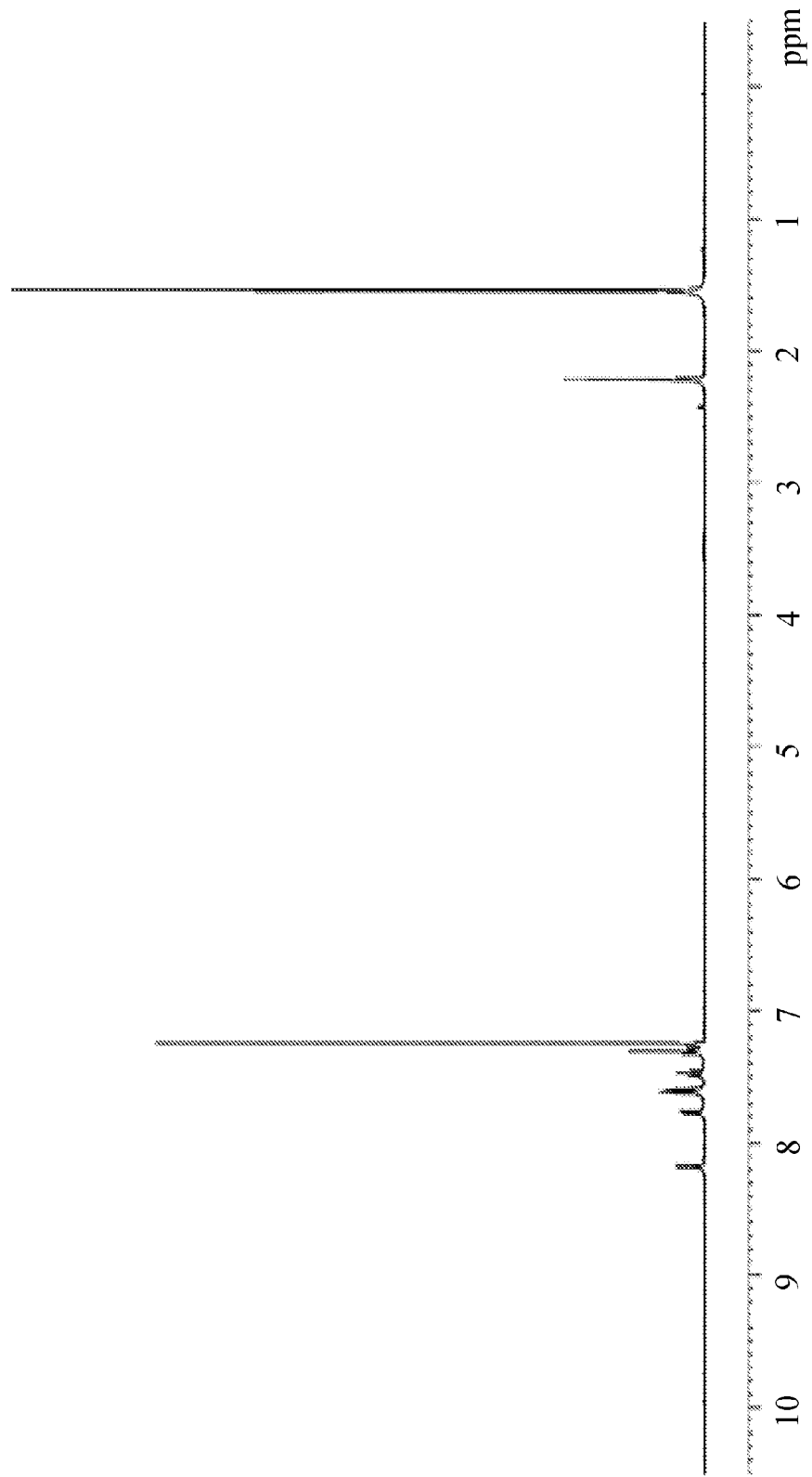
FIG. 3D is another ¹H NMR spectrum of EX1.
Figure 4D:
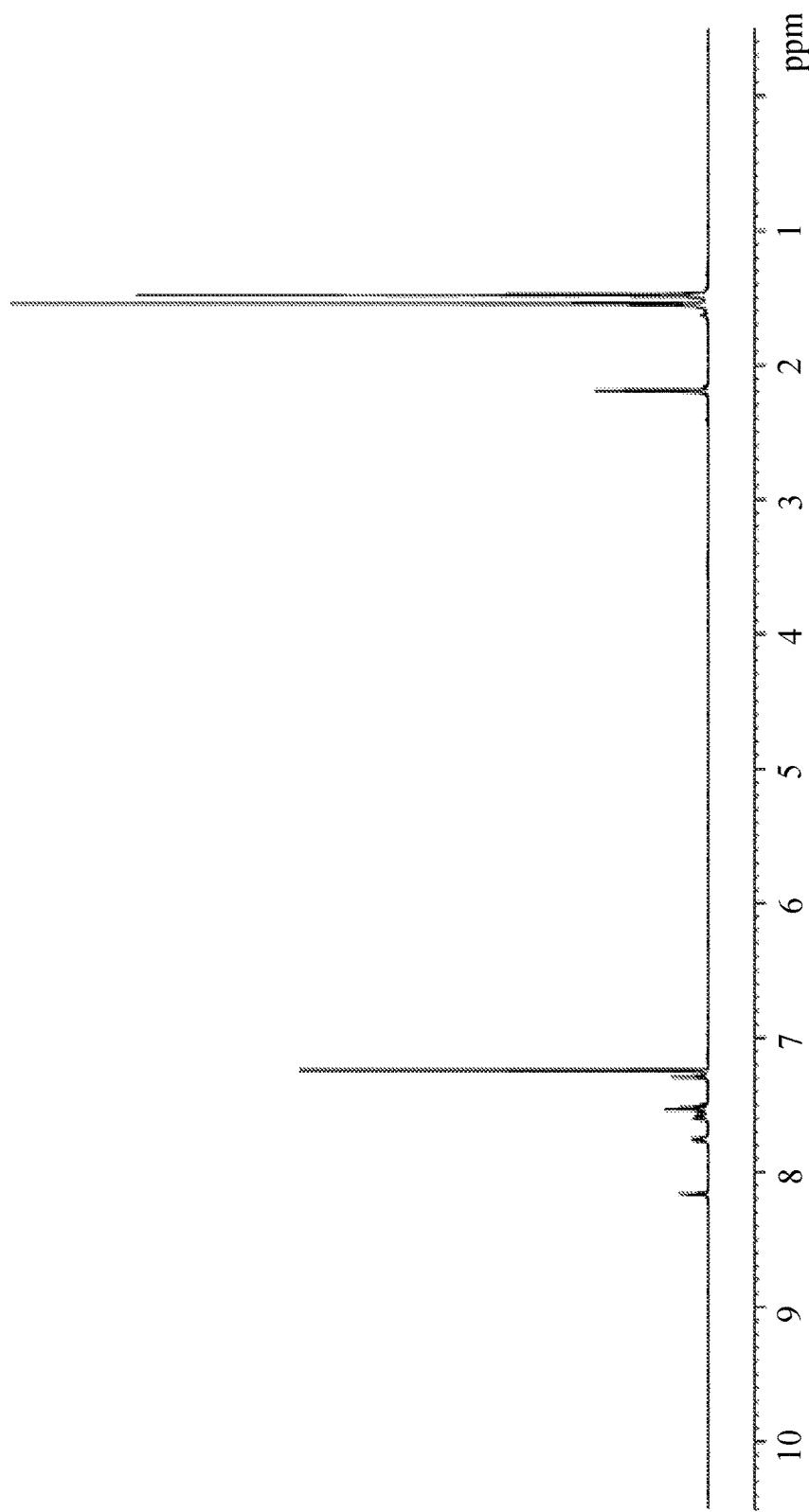
FIG. 4D is another ¹H NMR spectrum of EX2.
Figure 5D:
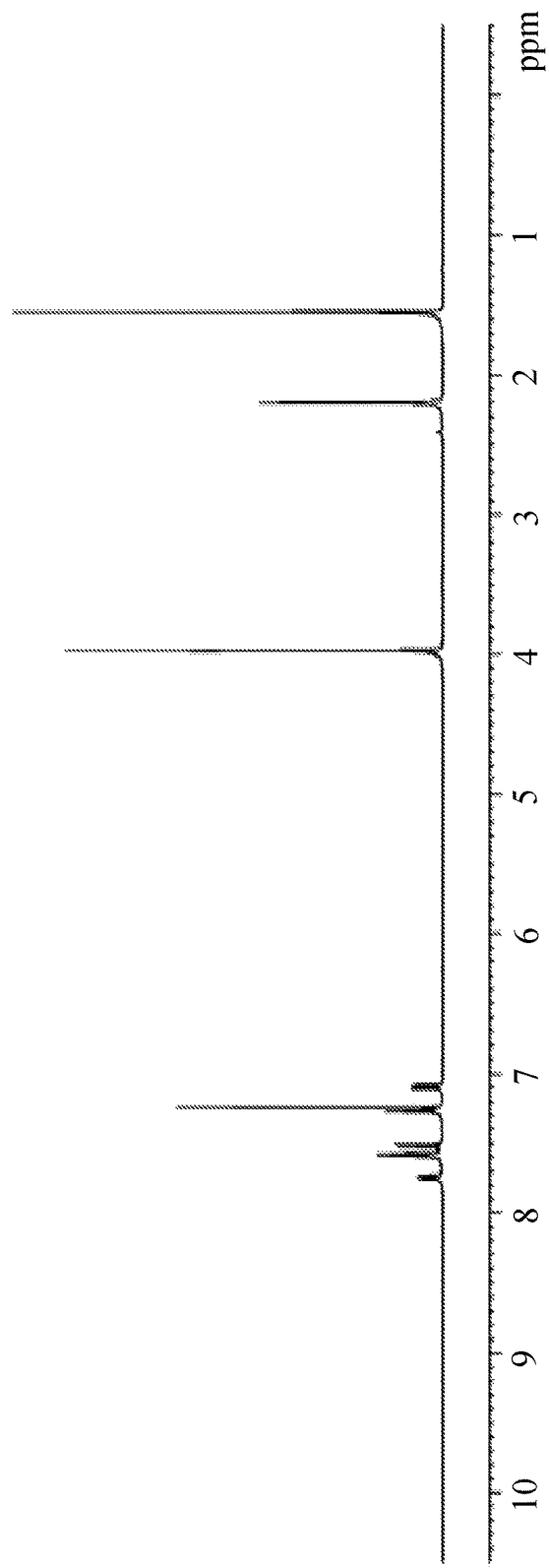
FIG. 5D is another ¹H NMR spectrum of EX3.
Figure 6D:
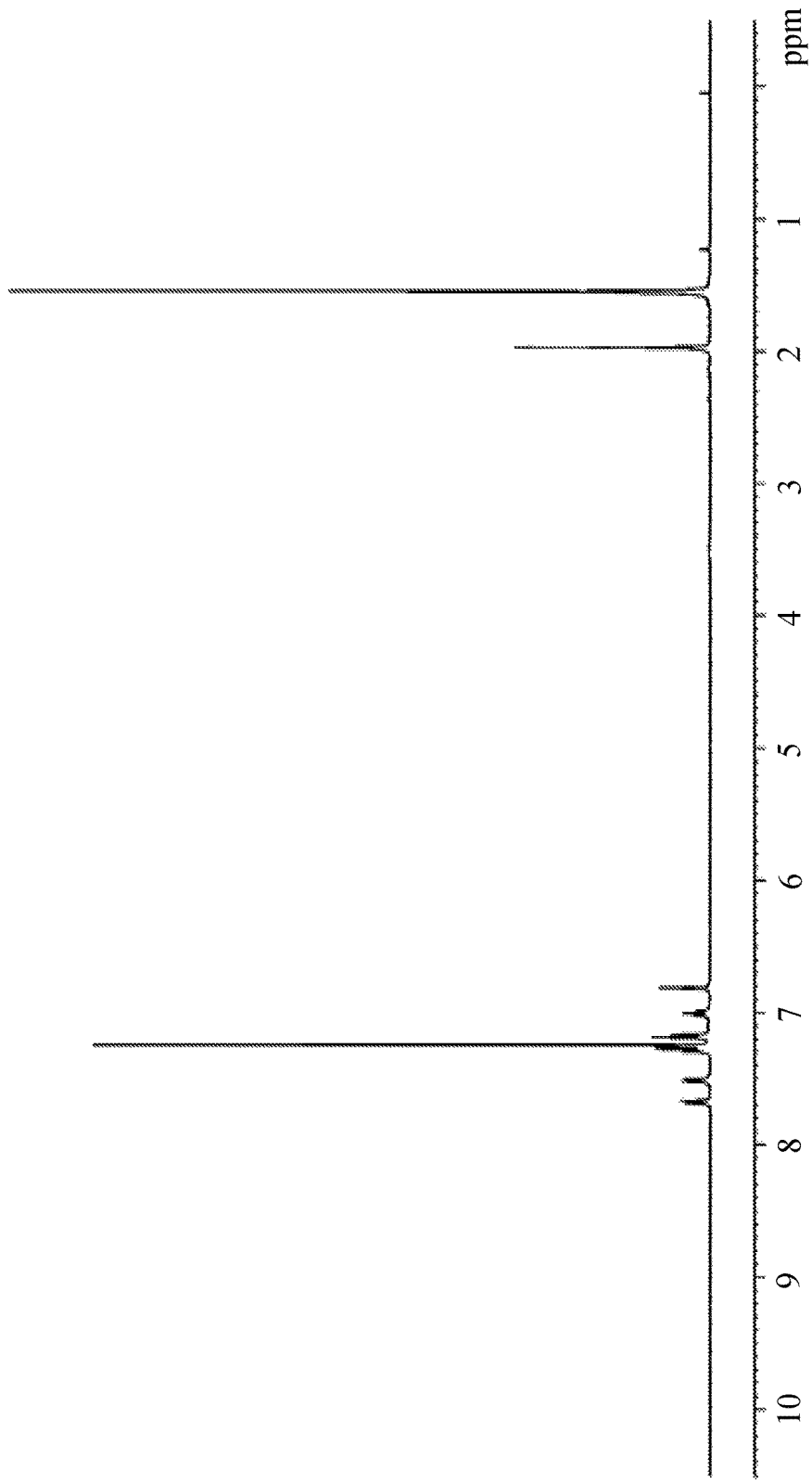
FIG. 6D is another ¹H NMR spectrum of EX4.

The boron-containing compounds of EX1 to EX4 are placed in an atmospheric environment for five months or more than five months. Then the $^1$H NMR spectra of EX1-EX4 are measured, respectively, from which can observe if the structures of the boron-containing compounds of EX1 to EX4 change in the atmospheric environment for five months or more than five months. Please refer to FIG. 3A and FIG. 3D at the same time, wherein FIG. 3A is the $^1$H NMR spectrum of EX1 measured on Jan. 3, 2016, and FIG. 3D is another $^1$H NMR spectrum of EX1 measured on Jun. 20, 2016. As shown in FIG. 3A and FIG. 3D, the structure of the boron-containing compound of EX1 does not change after being placed in the atmospheric environment for more than five months. Accordingly, the boron-containing compound of EX1 has excellent air/moisture stability. Please refer to FIG. 4A and FIG. 4D at the same time, wherein FIG. 4A is the $^1$H NMR spectrum of EX2 measured on Dec. 22, 2015, and FIG. 4D is another $^1$H NMR spectrum of EX2 measured on Jun. 20, 2016. As shown in FIG. 4A and FIG. 4D, the structure of the boron-containing compound of EX2 does not change after being placed in the atmospheric environment for more than five months. Accordingly, the boron-containing compound of EX2 has excellent air/moisture stability. Please refer to FIG. 5A and FIG. 5D at the same time, wherein FIG. 5A is the $^1$H NMR spectrum of EX3 measured on Jan. 31, 2016, and FIG. 5D is another $^1$H NMR spectrum of EX3 measured on Jun. 20, 2016. As shown in FIG. 5A and FIG. 50, the structure of the boron-containing compound of EX3 does not change after being placed in the atmospheric environment for almost five months. Accordingly, the boron-containing compound of EX3 has excellent air/moisture stability. Please refer to FIG. 6A and FIG. 6D at the same time, wherein FIG. 6A is the $^1$H NMR spectrum of EX4 measured on Dec. 19, 2015, and FIG. 6D is another $^1$H NMR spectrum of EX4 measured on Jun. 20, 2016. As shown in FIG. 6A and FIG. 6D, the structure of the boron-containing compound of EX4 does not change after being placed in the atmospheric environment for more than six months. Accordingly, the boron-containing compound of EX4 has excellent air/moisture stability.

OLED Devices Using Examples

OLED device A: the boron-containing compound (I-1-1) of EX1 is used as a dopant of an emitting layer of the OLED device A, and a doping concentration thereof is 10%. The OLED device A sequentially includes an anode, a hole injection layer, a hole-transporting layer, the emitting layer, an electron-transporting layer, an electron injection layer and a cathode. The structure of the OLED device A can refer to FIG. 2. The material and thickness of each layer of the OLED device A are as follows: ITO (130 nm)/NPB (40 nm)/TCTA (10 nm)/CBP:boron-containing compound (I-1-1) (10%) (30 nm)/TmPyPb (60 nm)/LiF (1 nm)/Al (100 nm).

OLED device B: the boron-containing compound (I-1-2) of EX2 is used as a dopant of an emitting layer of the OLED device B, and a doping concentration thereof is 10%. The OLED device B sequentially includes an anode, a hole injection layer, a hole-transporting layer, the emitting layer, an electron-transporting layer, an electron injection layer and a cathode. The structure of the OLED device B can refer to FIG. 2. The material and thickness of each layer of the OLED device B are as follows: ITO (130 nm)/NPB (40 nm)/TCTA (10 nm)/CBP:boron-containing compound (I-1-2) (10%) (30 nm)/TmPyPb (60 nm)/LiF (1 nm)/Al (100 nm).

OLED device C: the boron-containing compound (I-1-3) of EX3 is used as a dopant of an emitting layer of the OLED device C, and a doping concentration thereof is 10%. The OLED device C sequentially includes an anode, a hole injection layer, a hole-transporting layer, the emitting layer, an electron-transporting layer, an electron injection layer and a cathode. The structure of the OLED device C can refer to FIG. 2. The material and thickness of each layer of the OLED device C are as follows: ITO (130 nm)/NPB (40 nm)/TCTA (10 nm)/CBP:boron-containing compound (I-1-3) (10%) (30 nm)/TmPyPb (60 nm)/LiF (1 nm)/Al (100 nm).

OLED device D: the boron-containing compound (I-1-4) of EX4 is used as a dopant of an emitting layer of the OLED device D, and a doping concentration thereof is 10%. The OLED device D sequentially includes an anode, a hole injection layer, a hole-transporting layer, the emitting layer, an electron-transporting layer, an electron injection layer and a cathode. The structure of the OLED device D can refer to FIG. 2. The material and thickness of each layer of the OLED device D are as follows: ITO (130 nm)/NPB (40 nm)/TCTA (10 nm)/CBP:boron-containing compound (I-1-4) (10%) (30 nm)/TmPyPb (60 nm)/LiF (1 nm)/Al (100 nm). The structures of the compounds used in the OLED device A to the OLED device D are as follows:

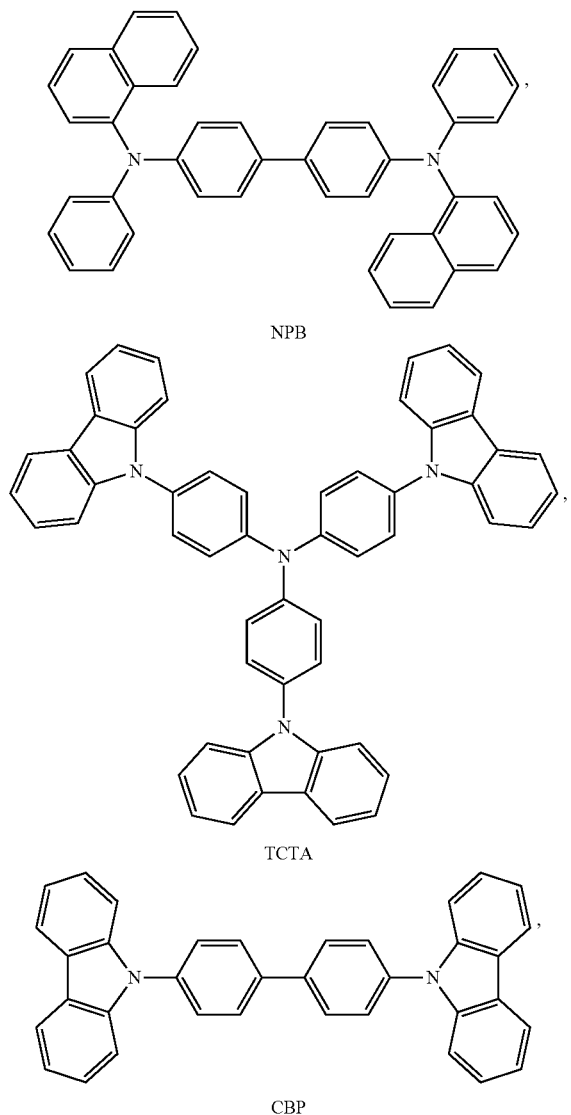

NPB

TCTA

CBP

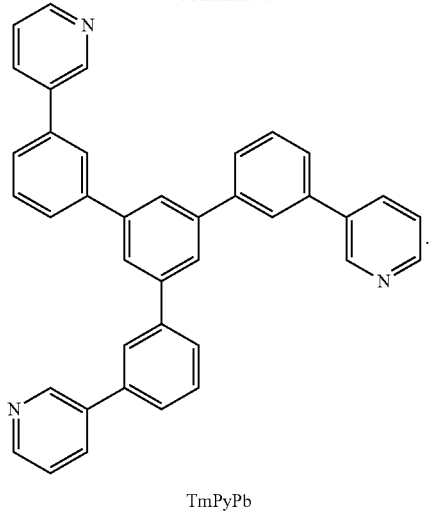

TmPyPb

Figure 10:
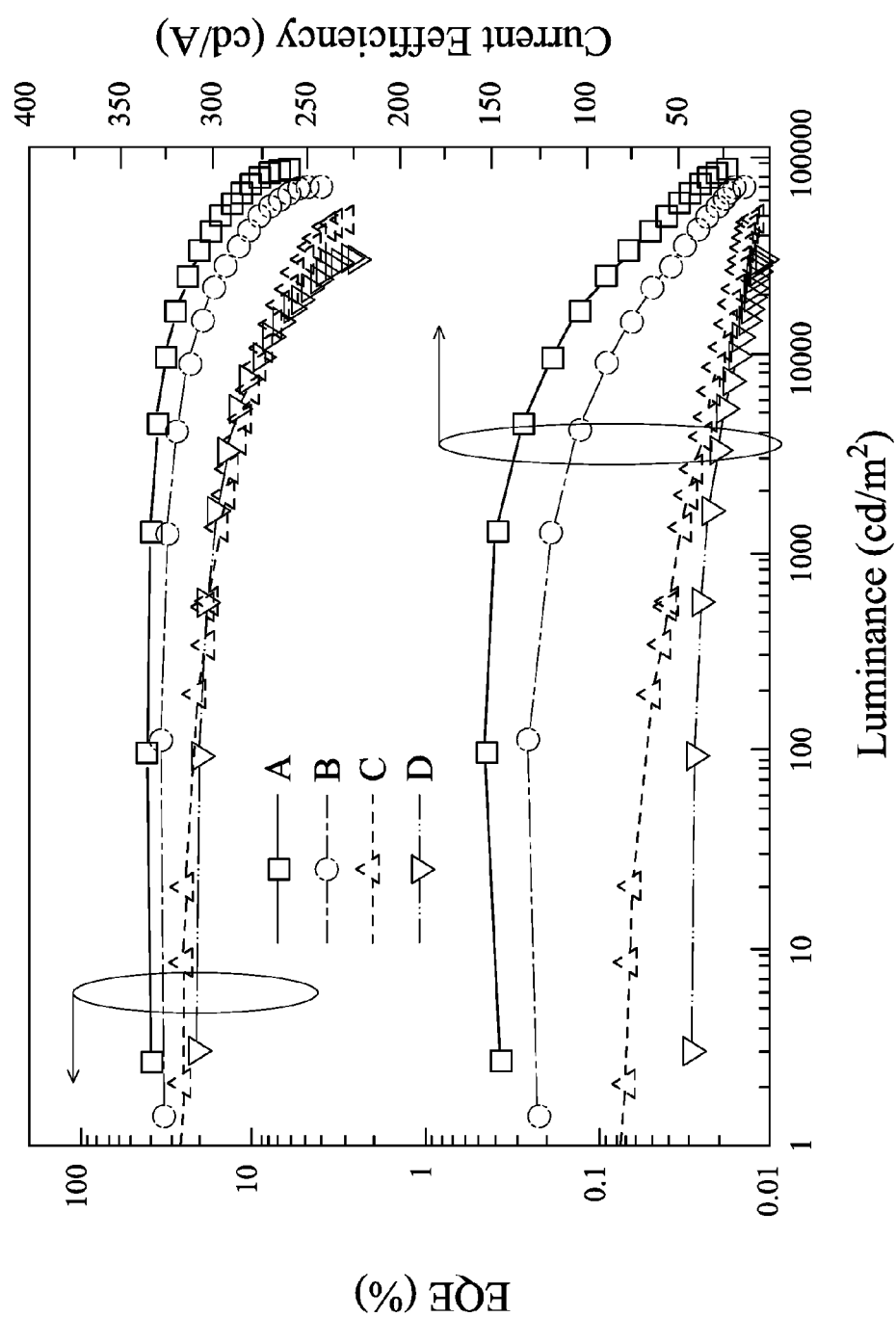
FIG. 10 shows relationships of EQE, current efficiency and luminance of OLED device A, an OLED device B, an OLED device C and an OLED device D.
Figure 11:
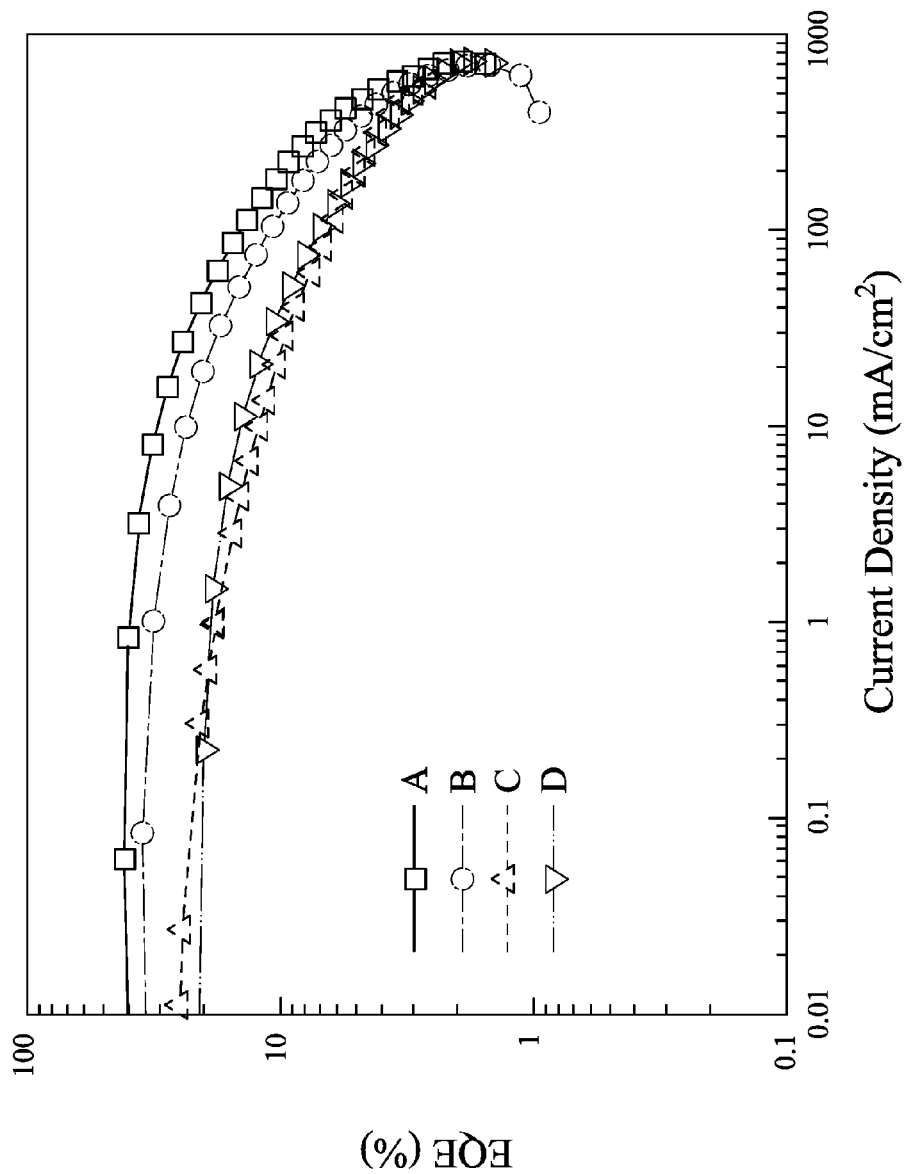
FIG. 11 shows relationships of EQE and current density of the OLED device A, the OLED device B, the OLED device C and the OLED device D.
Figure 12:
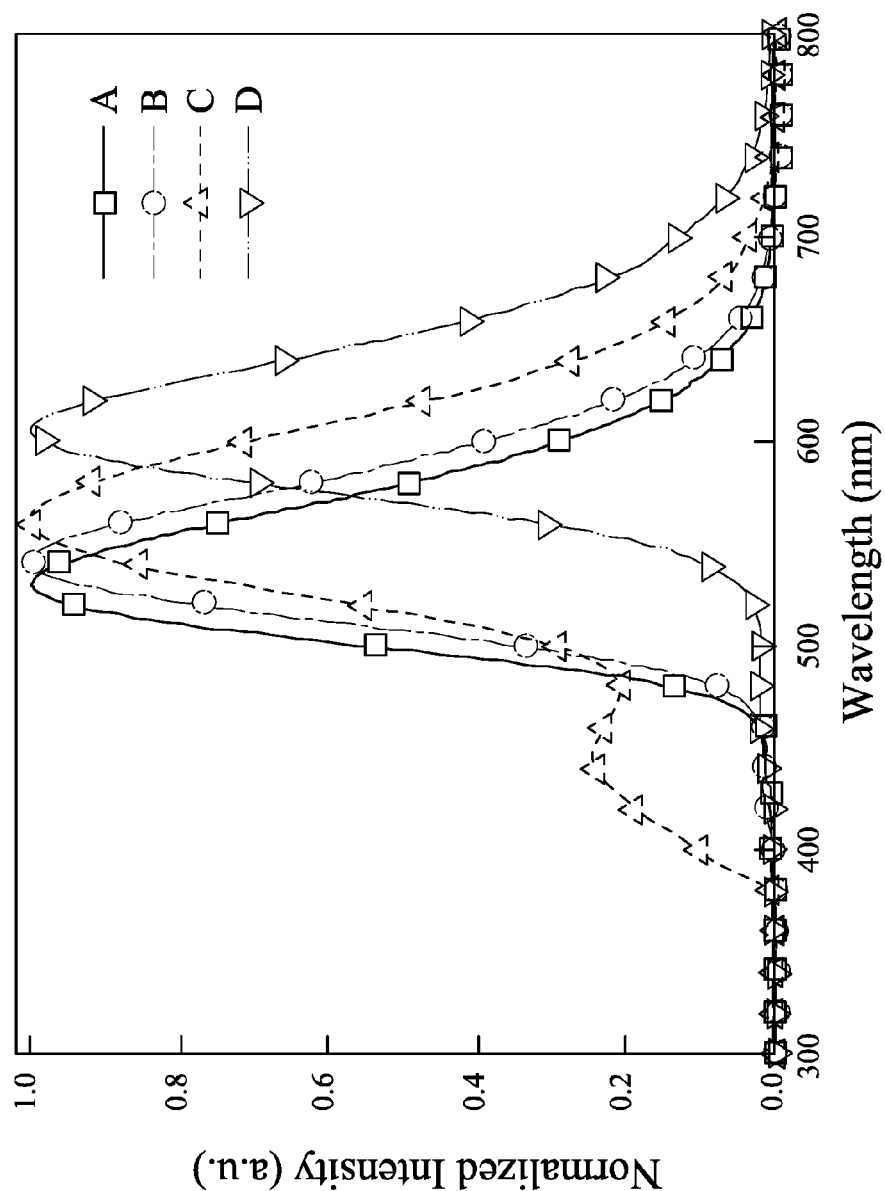
FIG. 12 shows electroluminescent spectra of the OLED device A, the OLED device B, the OLED device C and the OLED device D.

FIG. 10 shows relationships of EQE, current efficiency and luminance of the OLED device A, the OLED device B, the OLED device C and the OLED device D. FIG. 11 shows relationships of EQE and current density of the OLED device A, the OLED device B, the OLED device C and the OLED device D. FIG. 12 shows electroluminescent spectra of the OLED device A, the OLED device B, the OLED device C and the OLED device D. The turn on voltage ($V_d$), the maximum luminance (L) and the correspondent voltage, the maximum EQE ($\eta_{ext}$) and the correspondent voltage, the maximum current efficiency ($\eta_c$) and the correspondent voltage, the maximum power efficiency ($\rho_p$) and the correspondent voltage of each of the OLED device A to OLED device D are listed in Table 2, the maximum photoluminescence wavelength λ at 8 V and the chromaticity coordinate (CIE) of each of the OLED device A to OLED device D are listed in Table 3. The turn on voltage is also called the initial voltage, which is the voltage correspondent to the luminance of 1 cd/m². Moreover, the values of Table 2 and Table 3 are obtained first by measuring data with a silicon photodiode and a power measurement instrument (Keithley 2400 SourceMeter) and then by calculating the data according to efficiency formulas of OLED devices. The measuring methods and the efficiency formulas of OLED devices are conventional, and will not repeated herein.

TABLE 2

| OLED device | $V_d$ (V) | L (cd/m², V) | $\eta_{ext}$ (%, V) | $\eta_c$ (cd/A, V) | $\eta_p$ (lm/W, V) |
|---|---|---|---|---|---|
| A | 3.0 | 85791, 11.0 | 41.5, 3.5 | 154.2, 3.5 | 152.3, 3.0 |
| B | 3.0 | 69346, 11.0 | 35.1, 3.5 | 131.9, 3.5 | 131.6, 3.0 |
| C | 3.5 | 47446, 15.5 | 25.3, 3.5 | 77.8, 3.5 | 69.6, 3.5 |
| D | 3.0 | 30255, 12.0 | 21.1, 3.0 | 43.4, 3.0 | 45.3, 3.0 |

TABLE 3

| OLED device | λ at 8 V (nm) | CIE (x, y) |
|---|---|---|
| A | 530 | (0.33, 0.60) |
| B | 542 | (0.37, 0.58) |
| C | 562 | (0.39, 0.41) |
| D | 606 | (0.58, 0.41) |

As shown in Table 2, the maximum EQEs of the OLED device A to the OLED device D are all greater than or equal to 21.1%, wherein the maximum EQE of the OLED device A is high up to 41.5% and the maximum EQE of the OLED device B is high up to 35.1%, which shows that the boron-containing compounds according to the present disclosure are favorable to be used as the dopant in the emitting layers of the OLED devices, and can feature the OLED devices with excellent efficiency. Moreover, the boron-containing compounds according to the present disclosure are not like the phosphorescence materials requiring noble metals, so that the cost can be reduced. Furthermore, as shown in Table 3, the maximum photoluminescence wavelength λ at 8 V and the CIE of each of the OLED device A to OLED device D are different, which shows the OLED device A to OLED device D have different light colors. That is, the boron-containing compounds according to present disclosure can provide a wide light color tenability.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A boron-containing compound, comprising a structure of Formula (I):

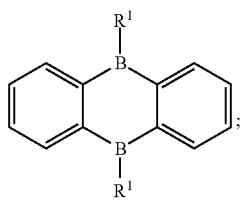
(I)

wherein each $R^1$ is independently a structure of Formula (i) or a structure of Formula (ii):

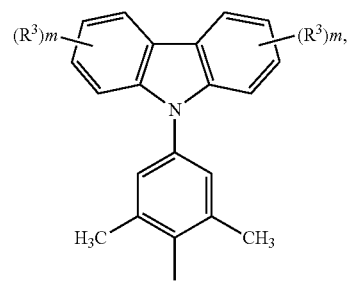
(i)

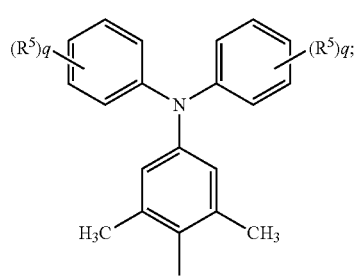
(ii)

wherein each m is independently an integer of 0 to 4, each q is independently an integer of 0 to 4, each $R^3$ is independently a methoxy group or a tert-butyl group, and each $R^5$ is independently a methoxy group or a tert-butyl group, and the boron-containing compound has thermally activated delayed fluorescence (TADF) property.

2. The boron-containing compound of claim 1, wherein each m is independently an integer of 0 or 1, each q is independently an integer of 0 or 1, and each $R^1$ is independently a structure of Formula (i-1-1), a structure of Formula (i-2-1), a structure of Formula (ii-1-1) or a structure of Formula (ii-2-1):

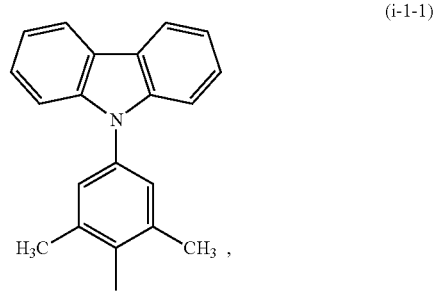
(i-1-1)

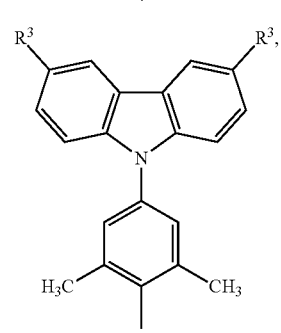
(i-2-1)

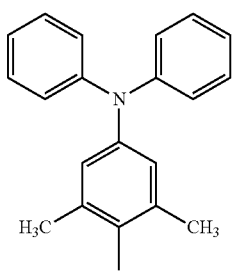
(ii-1-1)

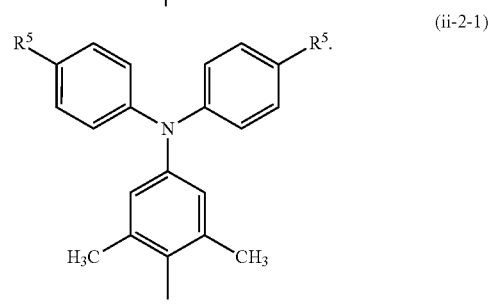
(ii-2-1)

3. An emitting layer of an organic light emitting diode (OLED), wherein the emitting layer comprises a dopant, and the dopant is a boron-containing compound comprising a structure of Formula (I):

(I)

wherein each R¹ is independently a structure of Formula (i) or a structure of Formula (ii):

(i)

(ii)

wherein each m is independently an integer of 0 to 4, each q is independently an integer of 0 to 4, each R³ is independently a methoxy group or a tert-butyl group, and each R⁵ is independently a methoxy group or a tert-butyl group, and the boron-containing compound has TADF property.

4. The emitting layer of the OLED of claim 3, wherein each m is independently an integer of 0 or 1, each q is independently an integer of 0 or 1, and each R¹ is independently a structure of Formula (i-1-1), a structure of Formula (i-2-1), a structure of Formula (ii-1-1) or a structure of Formula (ii-2-1):

(i-1-1)

(i-2-1)

(ii-1-1)

(ii-2-1)

5. The emitting layer of the OLED of claim 3, further comprising:

a host material comprising any one of structures of Formula (1) to Formula (9):

(1)

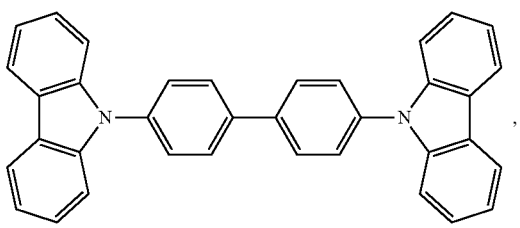
(2)
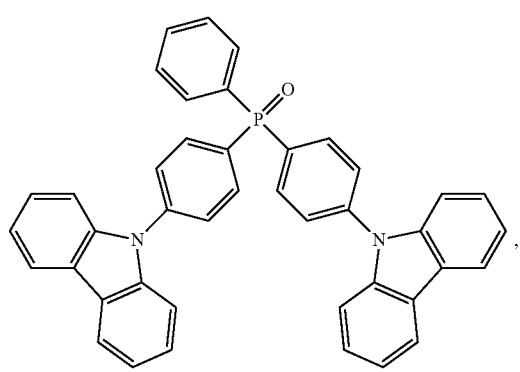
(3)
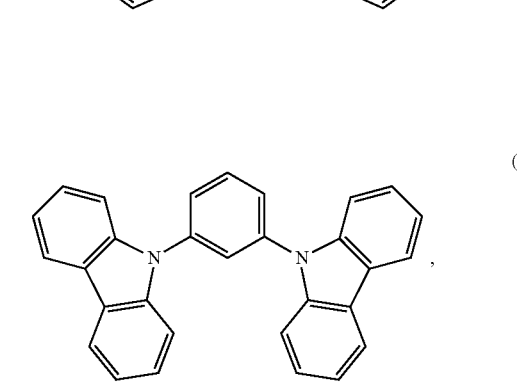
(4)
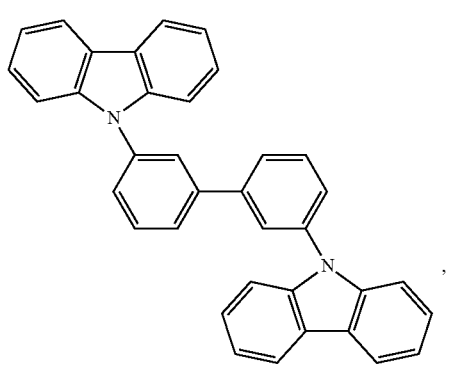
(5)
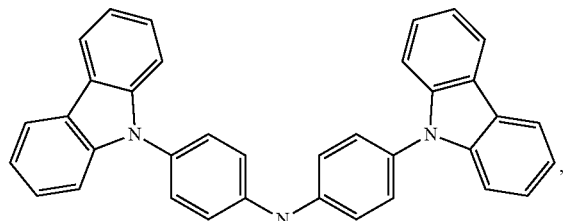
(6)
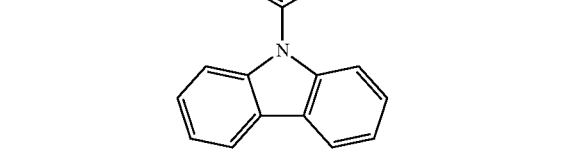
(7)
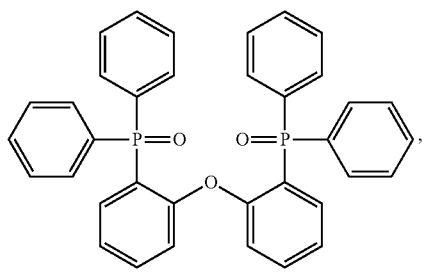
(8)
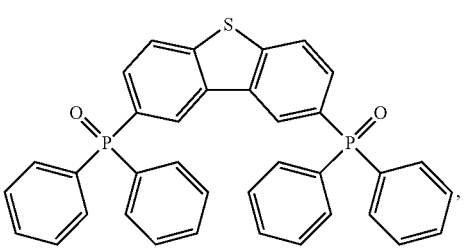
(9)
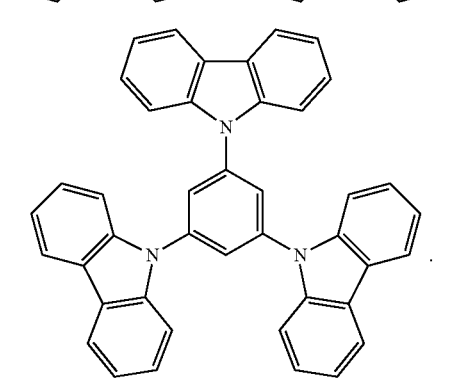
6. The emitting layer of the OLED of claim 3, wherein a doping concentration of the dopant in the emitting layer is in a range of 5% to 30%.
7. An OLED device, comprising:
the emitting layer of the OLED of claim 3.
* * * * *